(12) United States Patent
Dotor De Las Herrerías et al.

(10) Patent No.: US 12,078,633 B2
(45) Date of Patent: Sep. 3, 2024

(54) METHOD FOR PREDICTING AND MONITORING CLINICAL RESPONSE TO IMMUNOMODULATORY THERAPY

(71) Applicant: BIOHOPE Scientific Solutions for Human Health S.L., Madrid (ES)

(72) Inventors: Javier Dotor De Las Herrerías, Madrid (ES); Marianna Di Scala, Madrid (ES); Verónica Sánchez, Madrid (ES); Isabel Portero Sánchez, Madrid (ES)

(73) Assignee: BIOHOPE Scientific Solutions for Human Health S.L., Tres Cantos (ES)

( * ) Notice: Subject to any disclaimer, the term of this patent is extended or adjusted under 35 U.S.C. 154(b) by 127 days.

(21) Appl. No.: 17/501,784

(22) Filed: Oct. 14, 2021

(65) Prior Publication Data
US 2022/0283143 A1   Sep. 8, 2022

Related U.S. Application Data
(63) Continuation of application No. 16/019,279, filed on Jun. 26, 2018, now Pat. No. 11,175,282.

(30) Foreign Application Priority Data

Jun. 26, 2017 (EP) .................................. 17382399
Dec. 29, 2017 (EP) .................................. 17382923

(51) Int. Cl.
*G01N 33/50* (2006.01)
*C07K 16/28* (2006.01)
*G01N 33/574* (2006.01)
*C12N 5/078* (2010.01)

(52) U.S. Cl.
CPC ..... *G01N 33/5047* (2013.01); *C07K 16/2818* (2013.01); *G01N 33/57492* (2013.01);
(Continued)

(58) Field of Classification Search
CPC ......... G01N 33/57492; G01N 33/5047; G01N 33/5091; G01N 2800/245; G01N 2800/52; C07K 16/2818
See application file for complete search history.

(56) References Cited

U.S. PATENT DOCUMENTS 11,175,282 B2 *  11/2021  Dotor De Las Herrerías ............ G01N 33/57492
2010/0056390 A1 *  3/2010  Fischbach ............... C40B 60/08
506/10

(Continued)

FOREIGN PATENT DOCUMENTS

| WO | 2007/076061 A1 | 7/2007 |
| WO | 2011/078990 A1 | 6/2011 |
| WO | 2013/025543 A1 | 2/2013 |

OTHER PUBLICATIONS

Chan et al., "$Ca^{2+}$ released from calcium alginate gels can promote inflammatory responses in vitro and in vivo," *Acta Biomaterialia*: 2013 (11 pages).

(Continued)

*Primary Examiner* — Gailene Gabel
(74) *Attorney, Agent, or Firm* — SEED INTELLECTUAL PROPERTY LAW GROUP LLP

(57) ABSTRACT

The present invention provides a method to quantitatively measure the response of a patient to an immune-modulator drug that will aid clinicians in the determination of the optimal combination/posology of immunosuppressant/immune-modulator drugs. In addition, this method will open the possibility for clinicians to make the necessary adjustments in immunosuppressive therapy, as a way to avoid organ rejection to actually take place. Furthermore, this method will significantly reduce side effects of immunosuppressant drugs, optimizing therapeutic scheme and dosages, enabling the determination of the most effective immuno- (Continued)

suppression regimen at the lower dosages for each patient individually and monitoring of treatment efficiency along time, thus opening the door to treatment personalization.

13 Claims, 19 Drawing Sheets

(52) U.S. Cl.
CPC ........ *C12N 5/0634* (2013.01); *C12N 2533/54* (2013.01); *C12N 2533/76* (2013.01); *G01N 33/5091* (2013.01); *G01N 2800/245* (2013.01); *G01N 2800/52* (2013.01)

(56) References Cited

U.S. PATENT DOCUMENTS

| | | | |
|---|---|---|---|
| 2014/0273053 A1* | 9/2014 | Lee | C12M 23/12 435/25 |
| 2015/0101070 A1 | 4/2015 | Nam et al. | |
| 2017/0088814 A1* | 3/2017 | Thompson | C12N 5/0068 |

OTHER PUBLICATIONS

Higbee et al., "An Immunologic Model for Rapid Vaccine Assessment—A Clinical Trial in a Test Tube," *ATLA* 37(Suppl): 19-27, 2009.

Hoffmann et al., "NK Cells of Kidney Transplant Recipients Display an Activated Phenotype that Is Influenced by Immunosuppression and Pathological Staging," *PLOS ONE* 10(7):1-19, 2015.

Hou et al., "A human pluripotent stem cell platform for assessing developmental neural toxicity screening," *Stem Cell Research & Therapy* 4(Suppl 1):S12, 2013 (5 pages).

Mark et al., "Microfluidic lab-on-a-chip platforms: requirements, characteristics and applications," *Chem. Soc. Rev.* 39:1153-1182, Jan. 25, 2010.

Schwartz et al., "Human pluripotent stem cell-derived neural constructs for predicting neural toxicity," *PNAS* 112(40):12516-12521, 2015 (37 pages).

* cited by examiner

A

B

A

B

A

B

A

B

| Minimum | 0.0245971 +/- 0.0133 (54.09%) |
| Maximum | 0.406161 +/- 0.007122 (1.754%) |
| $IC_{50}$ | 4.44025 +/- 0.3977 (8.956%) |
| Hill coeff. | 2.606 +/- 0.6276 (24.08%) |

A

B

IMMUNOBIOGRAM – Mathematical SCORE

1. µ value – patient value for each point of the curve
2. Higher WEIGHT at point E∞
3. Sum of values of the corresponding subtraction (point 1)
4. Analysis of gaussian distribution of the results in point 3

METHOD FOR PREDICTING AND MONITORING CLINICAL RESPONSE TO IMMUNOMODULATORY THERAPY

FIELD OF THE INVENTION

The present invention relates to a method/kit suitable for carrying out a quantitative monitoring of the specific response of different patients to immunomodulatory drugs.

BACKGROUND OF THE INVENTION

There are many diseases in which the main pathogenic element is progressive chronic inflammation. Unlike the treatment of outbreaks of acute inflammation, which are easily controlled with current clinical management, the true workhorse of these diseases is to stop or reverse the process of chronic inflammation and progressive destruction of the tissue which follow successive acute outbreaks, with subsequent organ dysfunction or destruction of the affected organs with many clinical examples in this context, such as variants of progressive multiple sclerosis, rheumatoid arthritis, transplant rejection, and many others.

Chronic inflammation is associated with many human diseases, including autoimmune diseases, atherosclerosis, cancer and degeneration, among others. Inflammatory response, whatever the cause, its purpose is to eliminate the cause or return a tissue to a homeostatic state whether the malfunction was caused by an overload on the tissue or the organ. If the causes were transient (like after a trauma or certain infections), typically a resolution of the inflammatory phenomenon occurs, but if the cause is persistent or the immune system is unable to stop the response initiated, maintained pernicious response induces a sequence of changes in the immune system and affected tissue homeostasis which generally have been termed chronic inflammation. This is typical of autoimmune diseases, diseases which major pathogenic base is inflammation due to malfunction of the innate immune system or tolerance mechanisms (Crohn's disease) or constant immune stimuli (innate asthma, transplant organ rejection). In these cases, our physiological adaptive responses that supposedly offered a short-term benefit to eliminate the attack and repair tissue, become maladaptive to turn into chronic and induce destructive tissue changes, through appearance of fibrosis. Fibrosis is merely a response derived from a repeated adaptation to an adverse environment attempt (caused by whatever reason), which causes a strong stress on the tissue, impaired homeostasis and function, injury and therefore a need constant repair.

Chronic inflammation is a hardly reversible phenomenon which causes disabling injuries or end-organ disease. The real contribution of immunosuppressive/immunomodulatory drugs in diseases with an inflammatory or immunological substrate and associated chronic inflammation, is to restore a balance in the immune system or inflammatory state of patients, reversing the process and facilitating the development of repair mechanisms physiological tissue.

There are available a large number of medicines considered as immunosuppressants and immunomodulators in clinical medicine with diverse therapeutic applications. These are used in transplants, infectious diseases, inflammatory and autoimmune diseases, among others. It has been widely demonstrated the efficacy of these drugs to control acute outbreaks of inflammatory conditions. On the contrary, when the inflammatory phenomenon is entering a chronification state or has already achieved this phase, only some of these drugs and drug combinations are useful, and generally it can be only considered a partial success.

In the majority of inflammatory-based conditions, it is chronic inflammation and final fibrosis the real challenge. In the past years, a therapeutic approach based on clinical guidelines and avoidance of obvious adverse events in patients prone to them, has been enough to manage acute inflammatory outbreaks. This is based on the fact that all immunosuppressant drugs are quite effective in acute inflammation, so there is no need for a "fine tuning" of drug selection. But considering that immunosuppressive/immunomodulatory drugs are only partially effective in preventing and treating chronic conditions, a more robust approach to the selection of the most appropriate drug combination is needed. Currently, as will be explained below, there is no efficacy/potency tool to anticipate which drugs will be best for each patient, in a clinical scenario that needs urgently a better methodology to assist the physician to take the decision of what drugs/combinations should be used to treat each specific patient.

It was only through the discovery, evolution, and routine use of immunosuppressant medications that survival was increased and quality of life improved in many immune-based clinical conditions.

However, despite these glamorous advances, it is important to bear in mind the mechanism behind immunosuppression: immunosuppressants dampen the body's immune system which is essential for life, so it is critical to try a balance between efficacy to treat the clinical condition and not depressing the immune function too much, so severe adverse events may appear (infections and cancer).

Immunosuppressants target several cells of the immune system that show the following characteristics:
- They are blood-circulating, tissue resident or lymphoid organs cells.
- They are represented in what is called in laboratory standards "PBMCs" (Peripheral Blood Mononuclear Cells), easy to obtain from blood samples.
- They are cells capable of being "activated" under several stimuli which are termed "danger signals" in general: in infections are microorganism and virus molecules, in autoimmunity is a self-antigen, in transplantation it is the allogeneic tissue which drivers this activation, and in other conditions is a malfunction of the innate immune system or failure of tolerance mechanisms.
- After activation, they enter a quick clonal expansion phase, in which they exponentially divide.
- The resulting activated post-proliferation cells circulate to target tissue and enter an effector phase of attack, as killer cells or antibody-forming cells.

Immunosuppressants, at different points of the biochemical cascades that follow activation, inhibit clonal expansion thus preventing a huge number of effector cells articulate an attack to the target tissues. Nevertheless, it is essential to understand that not all patients respond the same to each immunosuppressants. Under these differences, we do not only find pharmacokinetic differences but also important pharmacodynamics differences. This means that there are differences in the PBMC response of different people to immunosuppressants, most probably based on genotype and epigenetic causes. In this sense, the specific HLA complex and other factors of each patient (genotype) as well as the specific immune profile at a certain point of time (epigenetic/phenotype), strongly influences the response to immunosuppressants.

Immunosuppression regimes vary from simple monotherapy treatments to very complex combinations implying the administration of cocktails combining up to 4-5 different drugs, as a way to ensure a maximum efficiency of immunosuppression. Currently, there is no personalized way to determine which drugs or drug combinations are more appropriate for each patient. The decision of which drugs to be used for a certain patient is based solely in two factors:
1) Clinical Guidelines: a summary of clinical trials performed with immunosuppressants are considered and reviewed by a panel of expert to write recommendations, indicating first-line and second-line treatments. This is based only on clinical trial results, which imply grouped statistical results of several cohorts of patients in a variety of countries, ages, times after disease onset, underlying disease and immune status. Thus, it is a valid for general recommendations, but clinical guidelines are not tools to determine which of the treatments would be better for a specific patient with a specific condition and immunological profile.
2) Adverse events frequently associated with drugs. Physicians choose drugs with an adverse event profile compatible with the biological and functional situation of the patient (like liver function, cardiovascular status, etc.). There are clinical tools to address this issue which work adequately for the objective.

This clinical management is clearly lacking a tool to determine the potency (efficacy) of immunosuppressant drugs over the immune cells of the patients, which are actually the target cells of the immunosuppressants/immunomodulators. This "potency assay" would identify those immunosuppressants that may be more efficacious for each patient at a certain point of time. A functional assay is needed because it is not possible to anticipate, for example based solely on pharmacogenetic studies, what will be the effect of immunomodulatory therapies over the immune system cells of a specific patient. Under the different responses of immunosuppressants there are many factors (genetic, epigenetic, etc.) that combined can only be sufficiently addressed with functional bioassays which address the final "immune response profile" of the patient at a certain point of time. Treatment regimens must be changed along a patient's life because the treatment efficiency varies over time as the immunological profile evolves over time in subsequent phases of the clinical condition (something similar like in antibiotic resistance with infections that prolong in time).

Currently, there is no way to determine the best immunosuppressant scheme for each patient but trial and error: physicians begin with some of the first-line drugs and if the clinical condition does not improve or even worsens, change to second-line drugs. This try and error approach entails a huge risk for the patient because if an error occurs, it can lead to the irreversible chronic inflammation and fibrosis of the tissue. For those patients who have to follow an immunosuppression therapy for long periods of time, efficacy would be improved and side effects could be reduced significantly if a rational approach is used in the selection of the optimal treatment for the specific patient needs (personalized treatment). This might be possible only by determining the effects of different therapies and therapy combinations in the "immune response profile" of the patient and monitoring the evolution along time, so medication adjustments could be made accordingly. However, as there is no solution available capable to do so, the personalized approach is impossible nowadays.

BRIEF DESCRIPTION OF THE INVENTION

The present invention provides a solution to the above mentioned problem by providing a tool/method to determine the efficacy of immunosuppressant and/or immunomodulator drugs over the immune cells of the patients, which are actually the target cells of the immunosuppressants/immunomodulators. In this sense, the present invention describes an in vitro bioassay that will provide an essential functionality for global clinical management of patients who need treatment with immunosupressors or immunomodulators, mainly for the treatment of chronic immune-based conditions. In particular, an immunobiogram to support clinicians in the determination of the optimal combination/posology of immunosuppressant/immunomodulator drugs to treat the inflammation while reducing risk of condition chronification and enabling a reduction of the undesired side effects of an ineffective immunosuppression (avoid under/over-immunosuppression).

In this regard, a blood sample extracted from a subject, in particular a human subject, by venipuncture will be processed to extract the PBMCs (for example, such sample processing can be performed by regular procedures widely used in clinical laboratories). These PBMCs will be stimulated for in vitro proliferation and separated in different fractions. Each fraction will be submitted (cell culture) to a different combination/posology of immunosuppressant/immunomodulators drugs (IMS potency assay). The PBMCs fractions cultured under these different conditions allows for a titration of the proliferation under each immunosuppresor/immunomodulatory drug and their combinations, which is a measure of the potency of these drugs over the target cells in each specific patient evaluated. The results of the analysis will generate an analytical report including: a) A hierarchy of immunosuppresants/immunomodulators drugs and combinations in order of inhibitory potency over target cells of the specific patient and b) recommendations for therapy adjustment individualized to each patient.

RFUs (%): fluorescent signal in relative fluorescent units (RFUs) normalized to 100% in the case of the positive control and 0% in the case of negative control. This signal indicates cell activation/proliferation, being maximum for the positive control and minimum for the negative control.

IMSs distance: represent the relative distance in a channeled well normalized from 0 to 100.

Limits of experimental signal detection are defined by:
C+: fluorescent signal generated by hydrogel containing cells (PBMC) previously activated.
C-: fluorescent signal generated by hydrogel containing inactivated cells (PBMC)

ID50 (inhibitory distance 50): refers to the relative distance at which inhibition of the drug over cellular activation reaches an effect of 50%. Taking into account that distance in the context of gradient diffusion indicates a certain concentration, this inhibitory parameter is equivalent to the concept of inhibitory concentration 50 (IC50), defined as the half maximal inhibitory concentration. This parameter is a measure of effectiveness of a substance in inhibiting a specific biological function (cell activation/proliferation in our case).

In addition, the rectangular figure in the lower side of the figure above represents a channel example (proportions definition described in the invention) containing pre-activated cells (as in the positive control C+), and also containing a delivery device loaded with an immunosuppressant drug (IMS) located at position 0.

Figure 23:
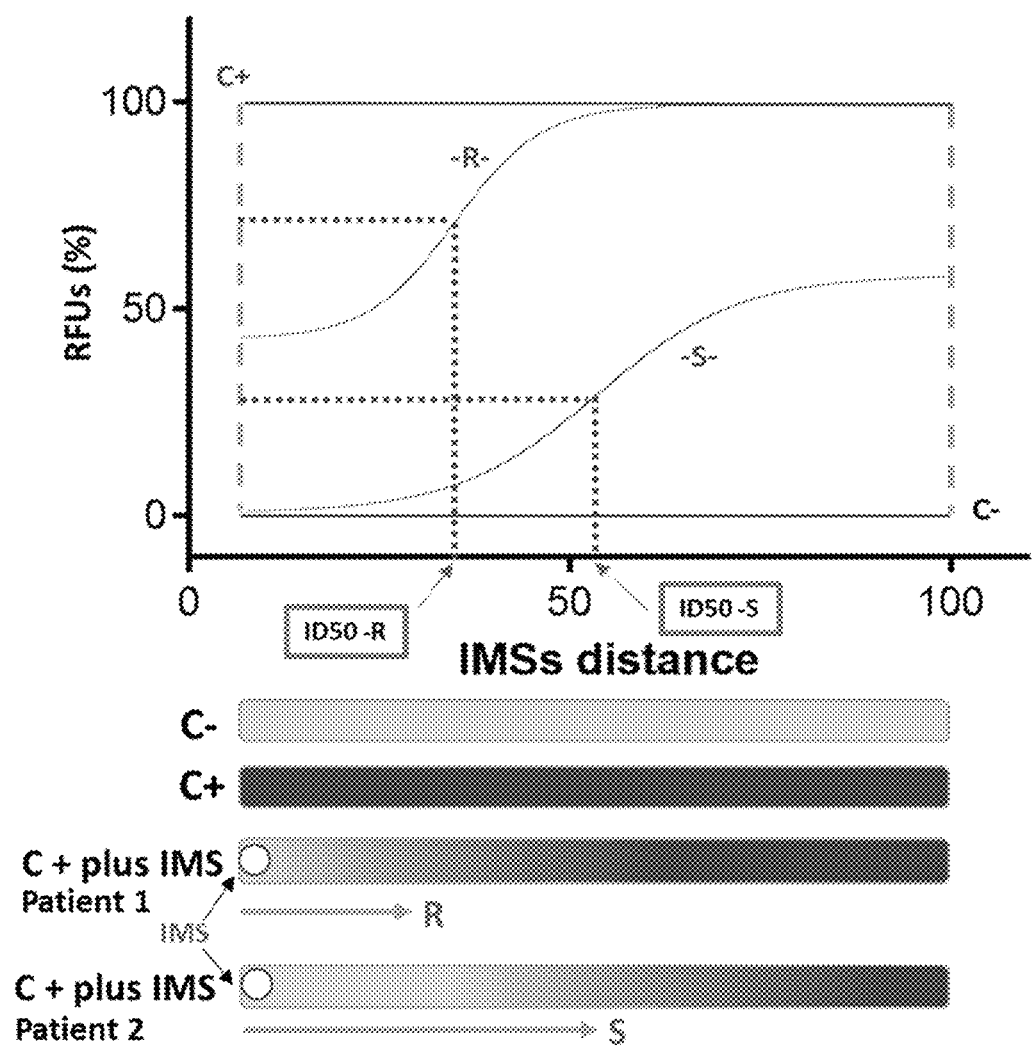

FIG. 23. This figure represents a diagram example of theoretical resistance and sensitive response of cells from two different patients to the same immunosuppressant drug gradient, resulting in two different hydrogel cells response patterns. The drug diffusion gradient is equivalent in both cases, but the cells included in the hydrogel generates different proliferative behaviour against the same comparative drug concentrations along de diffusion gradient.

Figure 24:
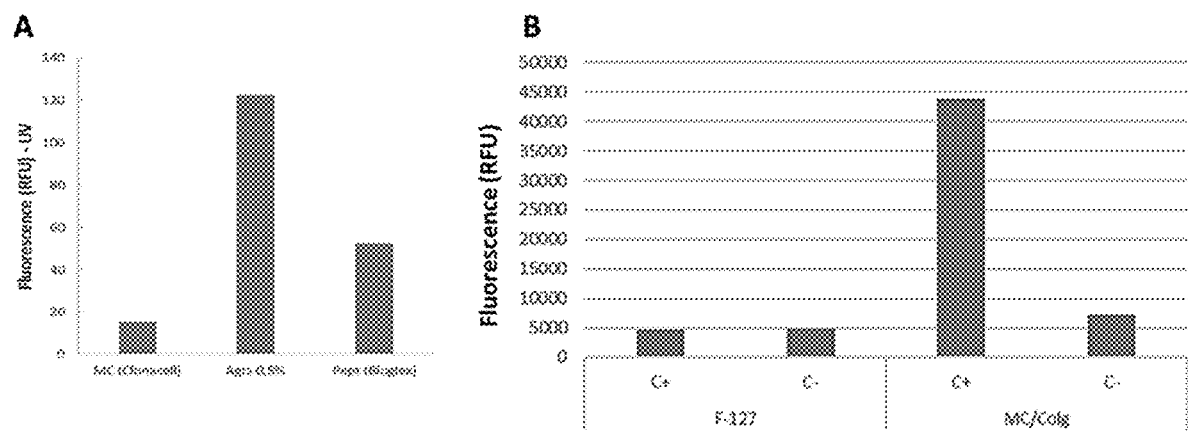

FIG. 24. This figure represents differences in hydrogels allowance for activated PBMCs proliferation. In figure A, the different proliferation rate of same donor derived activated PBMCs is represented. In this case agarose 0.5% is clearly a better cell environment for proliferation than methyl cellulose-clonacell and bioglex peptides. Figure B clearly shows how Pluronic hydrogel (F-127) is toxic and inhibits the proliferation of activated PBMCs (C+) compared with the optimized hydrogel composition of the copolymer (methyl cellulose/collagen).

Figure 25:
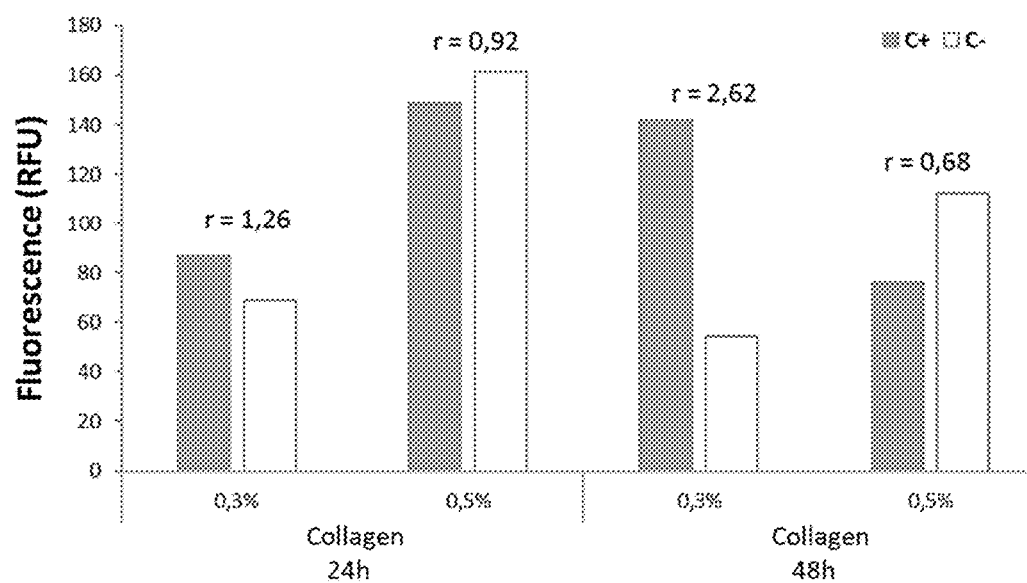

FIG. 25. This figure reflects the effect of a collagen hydrogel at 0.3% and 0.5%, and the evaluation is performed comparing positive and negative controls of PBMCs activation at two different time points. At early incubation time (24 h), collagen at 0.5% is able to induce a high and unspecific activation generating high levels of proliferation, measured as relative fluorescence; in both positive and negative controls. After 48 h of incubation, collagen at 0.3% allows the generation of an activation window, on the contrary 0.5% collagen induces a later inhibition of proliferation both in negative and positive control cells.

Figure 26:
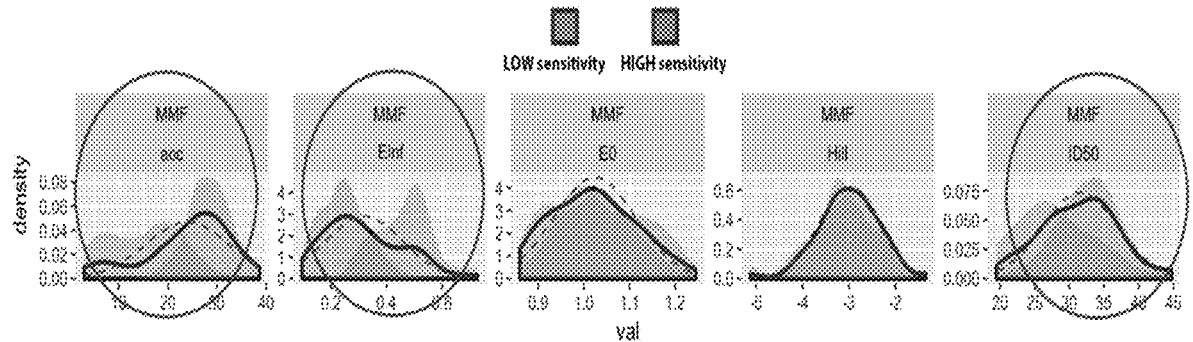

FIG. 26. Most discriminant parameters between LOW and HIGH sensitivity groups.

Figure 27:
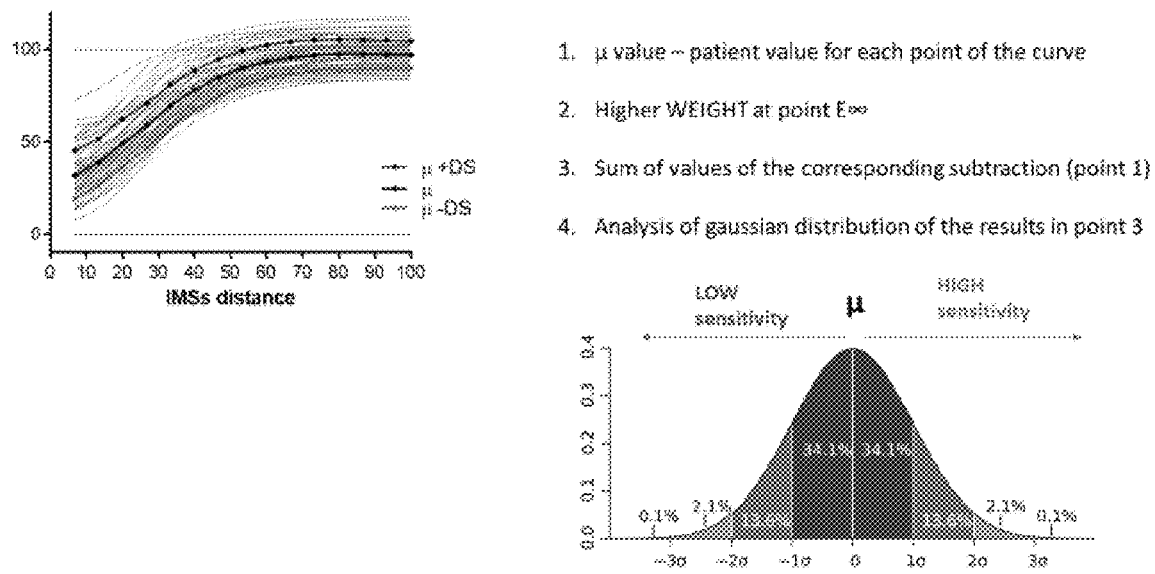

FIG. 27. Immunobiogram. Steps to established a mathematical score.

Figure 28:
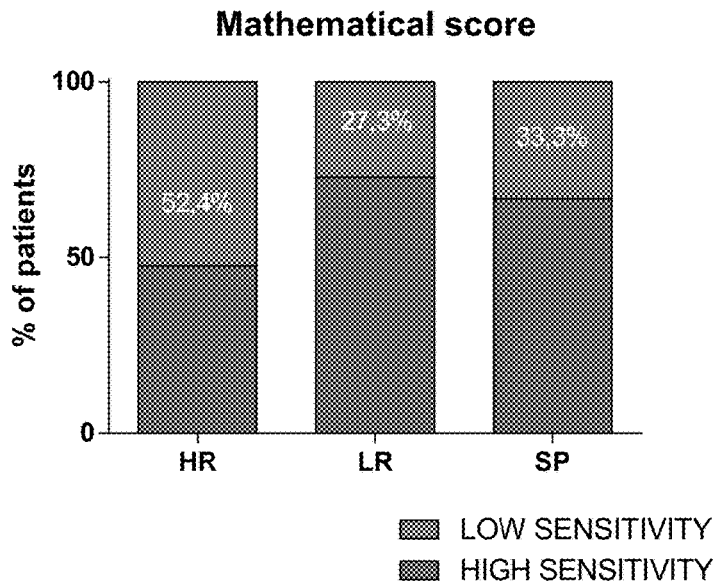

FIG. 28. Mathematical score.

Figure 29:
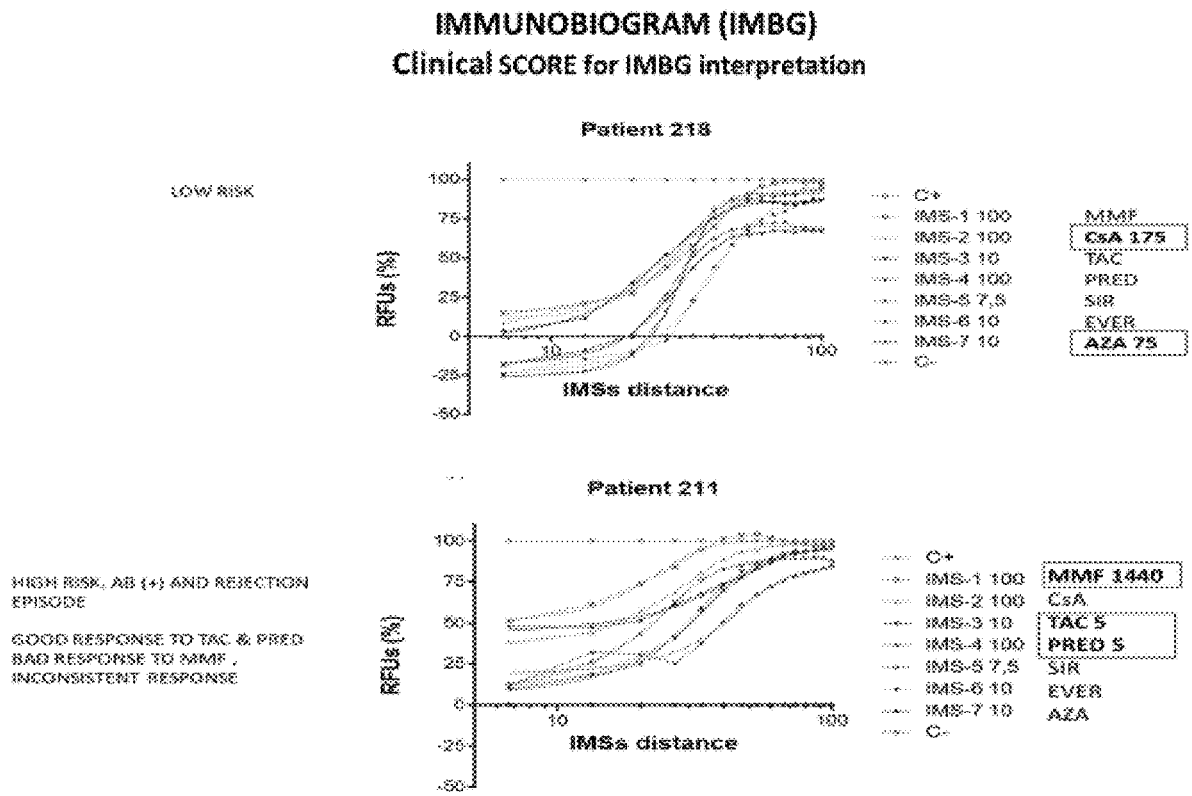

FIG. 29. Clinical score for IMBG interpretation.

Figure 30:
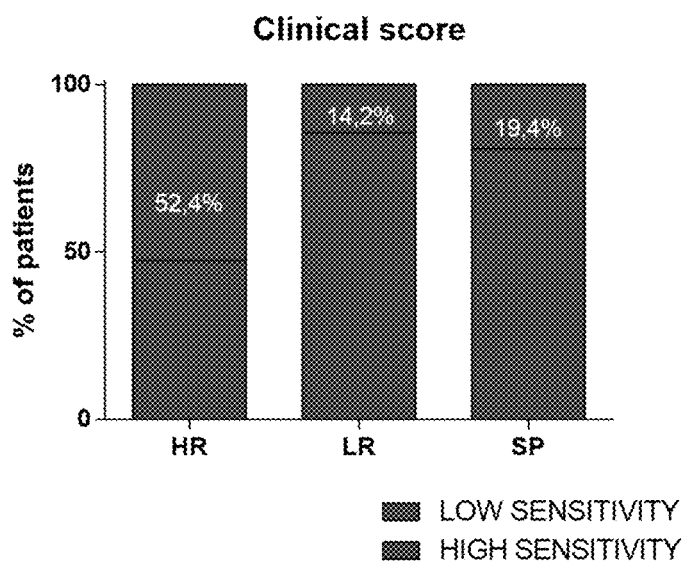

FIG. 30. Clinical score.

Figure 31:
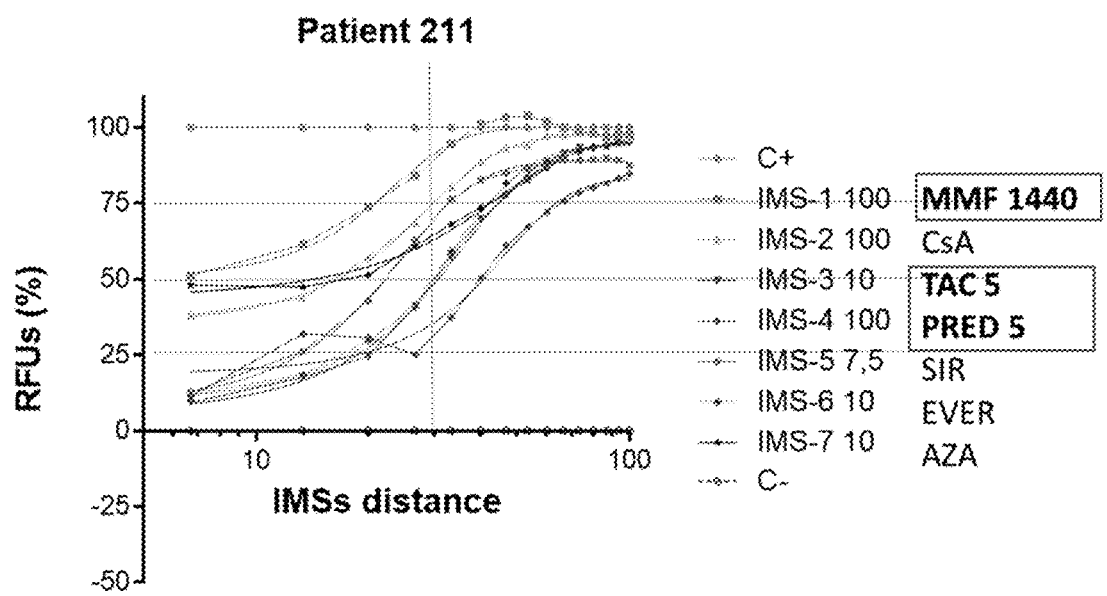

FIG. 31. Immunobiogram® graphic for patient 211.

DETAILED DESCRIPTION OF THE INVENTION

Definitions

As used herein the term "blood cellular derivatives" is understood as a population of total leukocytes, peripheral blood mononuclear cells or any specific sub-populations of PBMSc such as, but not limited to, T-lymphocytes, regulatory T cells (Tregs), NK (Natural Killer cells), macrophages or B-lymphocytes.

As used herein the term "cell culture collagen solution" is understood as an aqueous medium comprising salts and nutritional factors suitable to maintain the viability of PBMCs and a collagen percentage below 0.5% w/v, preferably equal or below 0.3% w/v.

As used herein the term "cell culture agarose solution" is understood as an aqueous medium comprising salts and nutritional factors suitable to maintain the viability of PBMCs and a agarose percentage equal or below 1% w/v, preferably below or equal to 0.5% w/v.

The term "about" in reference to a numeric value means+/−20% of that numeric value. The term "about" in reference to a numeric value also includes +/−10% of that numeric value. The term "about" in reference to a numeric value also includes +/−5% of that numeric value. The term "about" in reference to a numeric value also includes +/−1% of that numeric value.

The terms "comprise" and "comprising" are used in the inclusive, open sense, meaning that additional elements may be included. The term "comprises" also encompasses and may be used interchangeably with the terms "consists of" and "consists essentially of".

As used herein the term "immune-modulator drug or compound" is understood as any chemical compound (including any organic compound, recombinant or not proteins, antibodies, cytokines or any advanced therapy, including cell therapeutic products, gene products and any derivative) capable of inducing, increase, reduce or target the immune response. Examples of immune-modulator drugs are glucocorticoids (dexamethasone, prednisone, prednisolone, methylprednisolone, cortisone, hydrocortisone, triamcinolone, budesonide, etc), calcineurin inhibitors (cyclosporine A, Tacrolimus, etc), mTOR inhibitors (sirolimus, everolimus, and analogues), Cytokine/interleukin inhibitors (rilonacept, secukinumab, anakinra, isekizumab, tocilizumab, reslizumab, canakinumab, mepolizumab, basiliximab, siltuximab, daclizumab, faralimomab, elsilimomab, lebrikizumab, mepolizumab, etc), Antimetabolites (methotrexate, azathioprine, mycophenolic acid, leflunomide, terflunomide, etc), TNF-α inhibitors (etanercept, infliximab, certolizumab, golimumab, adalimumab, infliximab, pegsunercept, etc), recombinant interleukins (proleukin, oprelvekin, etc), CTLA-4 targets (abatacept, belatacept, ipilimumab, tremelimumab, etc), PD1/PDL-1 targets (Nivolumab, Pembrolizumab, etc), CD40/C40L targets (Teneliximab, Toralizumab), Cell therapy (Mesenchymal stem cells, regulatory T cells, Dendritic cells, etc) and others (lenalidomide, pomalizumab, thalidomide and derivatives, apremilast, etc) As used herein the term "immune-suppressant drug or compound" is understood as any organic compound, recombinant or not proteins, antibodies, cytokines or any advanced therapy, including cell therapeutic products, gene products and any derivative capable of targeting the immune response through reduction of immune cells activation, proliferation and/or inhibiting the effector responses.

As used herein the term "immune-modulator drug gradient" is understood as a substance distribution behaviour described by the Fick's diffusion laws where the solute will move from a region of high concentration to a region of low concentration across a liquid or semisolid spatial concentration gradient (first law) in a time dependent manner (second law). Fick's first law:

where

J is the "diffusion flux," of which $$J = -D\frac{d\varphi}{dx}$$

the dimension is the amount of substance per unit area per unit time, so it is expressed in such units as mol m$^{-2}$ s$^{-1}$. J measures the amount of substance that will flow through a unit area during a unit time interval.

D is the diffusion coefficient or diffusivity. Its dimension is area per unit time, so typical units for expressing it would be m$^2$/s.

φ (for ideal mixtures) is the concentration, of which the dimension is the amount of substance per unit volume. It might be expressed in units of mol/m$^3$.

x is position, the dimension of which is length. It might thus be expressed in the unit m.

$$\text{Fick's second law:} \frac{\partial \varphi}{\partial t} = D\frac{\partial^2 \varphi}{\partial x^2}$$

where

φ is the concentration in dimensions of [(amount of substance) length$^{-3}$], example unit mol/m$^3$; φ=φ(x,'t) is a function that depends on location x and time t;

t is time [s];

D is the diffusion coefficient in dimensions of [length$^2$ time$^{-1}$]; example unit m$^2$/s x is the position [length], example unit m As used herein the term "a cell culture solution capable of providing a hydrogel" is understood as an aqueous medium comprising salts and nutritional factors suitable to maintain the viability of PBMCs and a polymer capable of giving rise to a viscoelastic solid-like material comprised of an elastic cross-linked network and water, wherein water is the major component. It is noted that the polymer must be compatible with the 3D (three-dimensional) growth viability of PBMCs.

As used herein the term "lymphocyte activation compound" is understood as any chemical substance able to induce a lymphocyte cellular response such as cell proliferation, pro-inflammatory cytokines production and/or secretion, or membrane surface presentation of pro-activation receptors or ligands.

As used herein the term "agonistic antibodies anti CD3 (TCR) and CD28" is understood as any antibody able to specifically bind human CD3 and CD28 exerting an activation effect equivalent to the binding of the physiological membrane ligands MHC (Major Histocompatibility Complex) and CD80/86 respectively.

As used herein the term "ionomycin" is understood as a synthetic or bacterium *Streptomyces* conglobatu derived ionophore, able to raise the intracellular level of calcium (Ca2+) stimulating the lymphocytes intracellular production of interferon, perforin, IL-2, and IL-4. Usually used in conjunction with PMA.

As used herein the term "PMA (phorbol myristate acetate)" is understood as a chemical compound able to activate PKC (protein kinase C), and subordinated cell signalling responses that activates lymphocytes responses. Usually used in conjunction with ionomycin.

As used herein the term "lectins" is understood as any plant derived protein with high specific binding capacity to carbohydrates. Able to aggregate cell surfaces ligands and receptors inducing artificial lymphocyte cross stimulation.

As used herein the term "superantigens" is understood as any viruses or bacteria derived antigens able to induce a non-specific activation of T-cells resulting in polyclonal T cell activation and massive cytokine release.

As used herein the term "Lipopolysaccharides (LPS)", also known as lipoglycans or endotoxins, is understood as large molecules consisting of a lipid and a polysaccharide composed of O-antigen derived from the outer membrane of Gram-negative bacteria, able to elicit strong immune responses through activation of specific immune cells membrane surface receptors.

As used herein the term "antigen determinants or epitopes" is understood as part of an antigen that could be recognize by the immune system (antibodies, B cells or T cells).

As used herein the term "Mix Lymphocyte Reaction" is understood as is an ex vivo cellular immune assay reaction between two allogeneic lymphocyte populations (same species but genetically distinct donors) that induces lymphocyte proliferation and pro-inflammatory cytokines secretion in response to the major histocompatibility antigen (MHC Class I and II) differences between the two cell populations.

As used herein the term "efficacy" is understood as a drug's capacity to produce an effect on the target cells such as to induce a target cellular response consisting in modulating proliferation, production and/or secretion of immunoregulatory cytokines or factors, or membrane surface presentation of co-stimulatory receptors or ligands.

As used herein the term "embedded within the hydrogel" is understood as the activated PBMCs, total leukocytes or specific sub-populations of PBMCs fix into a surrounding hydrogel mass.

DESCRIPTION

The present invention provides a method to quantitatively measure the response of a patient to an immune-modulator drug that will aid clinicians in the determination of the optimal combination/posology of immunosuppressant/immune-modulator drugs. In addition, this method will open the possibility for clinicians to make the necessary adjustments in immunosuppressive therapy, as a way to avoid organ rejection to actually take place. Furthermore, this method will significantly reduce side effects of immunosuppressant drugs, optimizing therapeutic scheme and dosages, enabling the determination of the most effective immunosuppression regimen at the lower dosages for each patient individually and monitoring of treatment efficiency along time, thus opening the door to treatment personalization.

As stated above, the present invention provides a method to titrate the response of a patient to an immune-modulator drug, wherein such titration shall aid clinicians in the determination of the optimal combination/posology of immunosuppressant/immune-modulator drugs. In addition, this method will open the possibility for clinicians to make the necessary adjustments in immunosuppressive therapy, as a way to avoid organ rejection to actually take place.

In order to correctly understand the present invention, is important to note that the term "titration" should be understood as the quantitative analysis of the dose dependent effect of an immunosuppressant based on the generated gradient in a hydrogel. It is further important to note that in the present invention we titrate the effect (not the concentration) of the immunosuppressants, by analysing how a immunosuppressant progressively loses its capacity to damper cell proliferation because of its continuously diminished concentration thorough a channel, being the channel homogeneously filled by activated proliferating immune cells, so this inhibitory capacity is higher in the extreme of the channel where the concentration is higher and inhibition is progressively diminished thorough the channel as the immunosuppressant concentration lessens.

Consequently, in the present invention we analysed the spatial gradient formed through the channel over the hydrogel embedded cells proliferation/activation. In order to determined such titration of the immunosuppressant drugs, in the method of the present invention, the immunosuppressant's dose is controlled in the dry amount included in the discs that are inserted in the hydrogel, after inserting the discs in the hydrogel, a concentration gradient is generated by diffusion of the immunosuppressant and such gradient generates a dose dependent effect over the cells embedded within the hydrogel that is, afterwards, revealed and measured as a fluorescence signal with a fluorimeter.

Figure 22:
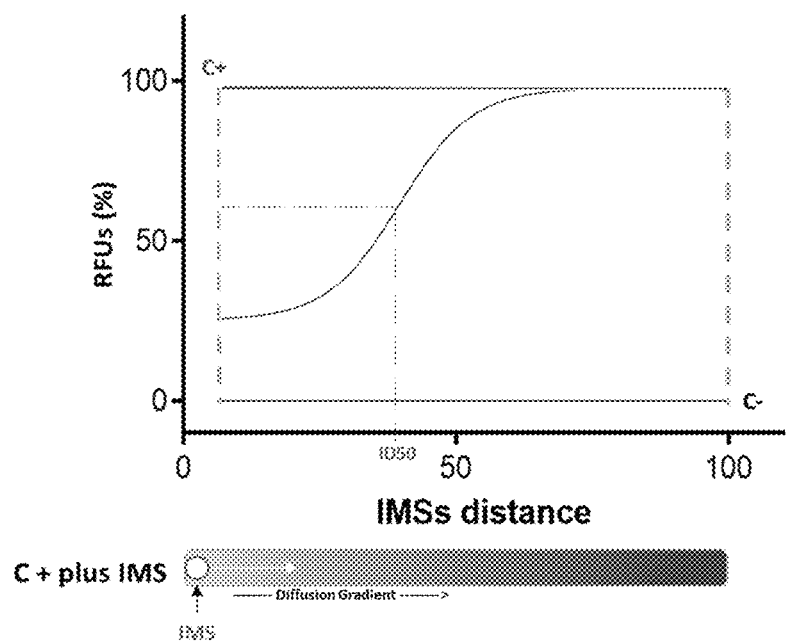
FIG. 22. This figure is a graphical representation of the process describe in the claims. In particular, it represents the titration of a stable immunosuppressant drug gradient effect generated through spontaneous diffusion of the drug in a hydrogel, over the activation/proliferation status of the cells contained within. The axis of the graph represents.

In order to aid the reader understanding the invention as defined in the claims, we refer to the graphical description of the invention rationale as illustrated in FIG. 22. This figure is a graphical representation of the process describe in the claims. In particular, it represents the titration of a stable immunosuppressant drug gradient effect generated through spontaneous diffusion of the drug in a hydrogel, over the activation/proliferation status of the cells contained within. The axis of the graph represents:

RFUs (%): fluorescent signal in relative fluorescent units (RFUs) normalized to 100% in the case of the positive control and 0% in the case of negative control. This signal indicates cell activation/proliferation, being maximum for the positive control and minimum for the negative control.

IMSs distance: represent the relative distance in a channeled well normalized from 0 to 100.

Limits of experimental signal detection are defined by:

C+: fluorescent signal generated by hydrogel containing cells (PBMC) previously activated.

C−: fluorescent signal generated by hydrogel containing inactivated cells (PBMC)

ID50 (inhibitory distance 50): refers to the relative distance at which inhibition of the drug over cellular activation reaches an effect of 50%. Taking into account that distance in the context of gradient diffusion indicates a certain concentration, this inhibitory parameter is equivalent to the concept of inhibitory concentration 50 (IC50), defined as the half maximal inhibitory concentration. This parameter is a measure of effectiveness of a substance in inhibiting a specific biological function (cell activation/proliferation in our case).

In addition, the rectangular figure in the lower side of the figure above represents a channel example (proportions definition described in the invention) containing pre-activated cells (as in the positive control C+), and also containing a delivery device loaded with an immunosuppressant drug (IMS) located at position 0. Once the delivery device is placed in the hydrogel, the IMS loaded in the device at position 0 starts to spread (process of diffusion) through the hydrogel exerting an anti-proliferative and inactivated effect over the cells resulting in a dose dependent titration based on the generated stable gradient diffusion in the hydrogel. Red colour represents the fluorescent signal of activated cells, pale blue colour represents low or absent fluorescent signal produce by inactivated cells or cells inhibited by the immunosuppressant presence. In the channel that includes the activated cells within a hydrogel and plus the device loaded with the immunosuppressant drug (C+ plus IMS), colour transition from pale blue to red in the channel represents the diffusion gradient of the IMS that ranges from total cell activation inhibition close to position 0 (IMS delivery device) to lack of inhibition in the opposite side of the channel.

In addition, in order to further aid the reader understanding the invention as defined in the claims, we refer to the graphical description of the invention rationale as illustrated in FIG. 23. This figure represents a diagram example of theoretical resistance and sensitive response of cells from two different patients to the same immunosuppressant drug gradient, resulting in two different hydrogel cells response patterns. The drug diffusion gradient is equivalent in both cases, but the cells included in the hydrogel generates different proliferative behaviour against the same comparative drug concentrations along de diffusion gradient.

Therefore, as illustrated above, the system of the present invention is capable of differentiating at least two different profile responses from two different patients, of relative resistance (R) or sensitivity (S) to the same immunosuppressant drug. Based on a constant gradient of drug diffusion through a standardized hydrogel, patient's cells (patient 2) with high sensitivity to a particular immunosuppressant drug provide a higher inhibitory profile that correlate with a higher ID-50 (S); on the contrary patient's cells (patient 1) with high resistance (R) to the same drug immunosuppressant's effect shall maintain a higher cell activation at higher concentrations of the drug (close to de IMS initial point of diffusion), thus providing a lower ID50.

In order to generate such a concentration gradient by diffusion of the immunosuppressant, there are thus three essential elements:

1. First, non-circular wells defined as channeled wells or channels characterized by a dimensional proportion in which one of the spatial three axes (longitudinal axis) is at least 4 times longer than the length average of the two other axes, must be use. Only by using such channeled wells we were able to conform a hydrogel shape, so that the hydrogel introduced therein (in the channeled well) was capable of providing a measurable and stable drug gradient flux in the longitudinal axis of described channeled well.
2. Second, the hydrogel introduced therein must comply with certain characteristics that includes biocompatibility with cell culture, toxicity-free, adequate and controllable stiffness over assay running time and consistent operability with the requirement of each assay step.
3. Third, immunosuppressive drug diffusion into the hydrogel must be the generated from a dry, concrete quantity deposited at the edge of a channeled well in a device or formulation capable of deliver the product into the hydrogel through a passive diffusion process. This experimental step enables the standardization requirements of the invention and overcomes the solubility issues related with the majority of immunomodulatory drugs.

As regards the first essential element described above, it is noted that the method described in the claims fails to work efficiently with a standard well of a microplate, since large dimension standard wells plates (6-12 wells plates) are not able to generate immunosuppressant multi-screening data, and reduced dimension well plates (24 to 1536) are not able to generate a measurable immunosuppressant gradient. Only with non-circular wells defined as channeled wells or channels characterized by a dimensional proportion in which one of the spatial three axes (longitudinal axis) is at least 4 times longer than the length average of the two other axes we were able to conform a hydrogel shape, so that the hydrogel introduced therein (in the channeled well) was capable of providing a measurable and stable drug gradient flux in the longitudinal axis of described channeled well. The length mean or average of the two minor axes is defined as the sum of lengths divided by 2. It is important to note that for such measurable and stable drug gradient flux to be produced in the longitudinal axis of the described channeled well, the channeled well should be covered completely by the hydrogel in its longitudinal axis and should covered at least a 30% of the channeled well height.

In this sense, in the context of the present invention "standard well" is understood as any well, included in the dimensional definition of cylindric or equilateral quadrangular wall; rounded, conical or flat bottom; 1.5 to 35 mm of diameter or side, 5 to 20 mm of height and 10 to 16,800 ul of total volume. Standard wells also include procedures or microplate devices able to generate hanging drops of liquid culture media or hydrogels drop/pieces that can be framed in the standard well mentioned dimensions.

Figure 16:
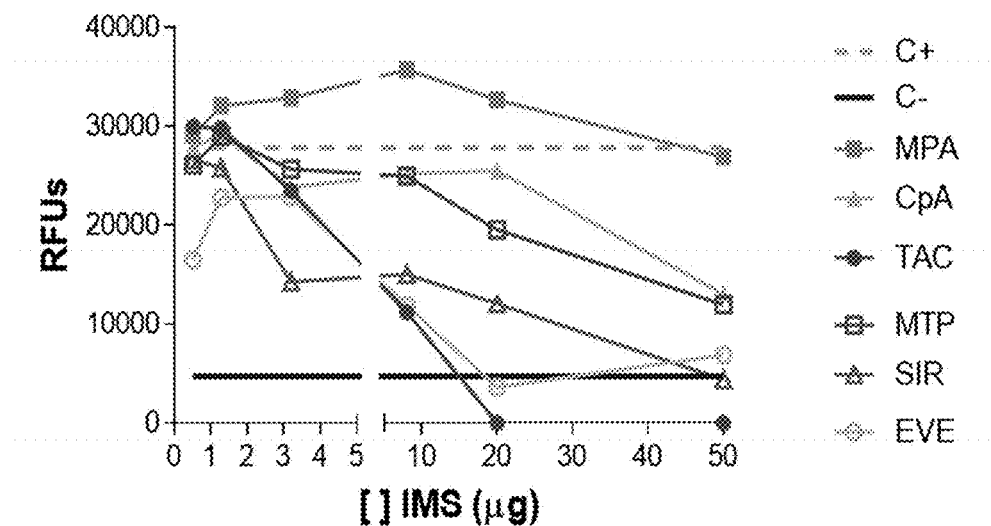
FIG. 16. Titration of immunosuppressant loaded discs effect with different doses over human activated PBMC, included in copolymer hydrogel Collagen-Methyl cellulose in 48 wells microplate (A). Gradient effect of discs loaded with 20 or 50 micrograms of immunosupressants inside the wells was measured and represented as function of distance from disc position (B). C+: positive control (PBMC stimulated with dynabeads); C-: negative control (unstimulated PBMC); MPA=Mycophenolic Acid; CpA=Cyclosporine A; TAC: tacrolimus; MTP. Methyl Prednisolone SIR: Sirolimus; EVE=Everolimus. RFU: Relative Fluorescence Units.
Figure 16:
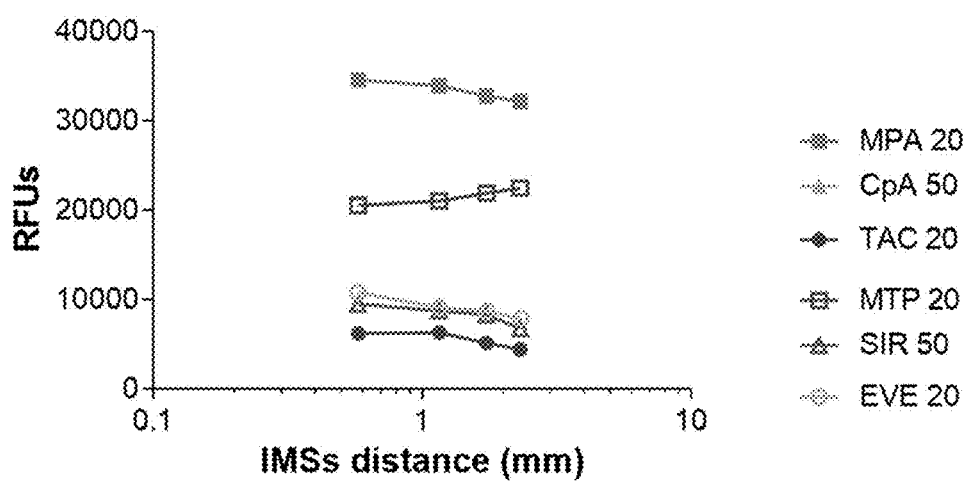

In order to demonstrate that the method described in the claims fails to work efficiently with a standard well of a microplate, since large dimension standard wells plates (6-12 wells plates) are not able to generate immunosuppressant multi-screening data, and reduced dimension well plates (24 to 1536) are not able to generate a measurable immunosuppressant gradient, please refer to examples 1 to 5 and, in particular to FIG. 16. In particular, it is clear from the result shown in FIG. 16B that the gradients generated in reduced dimension standard wells are not sufficient to adequately titrate the effect of an immunosuppressive drug on the hydrogel embedded cells. From these results, it is clearly derived that in reduced dimension standard wells with equitable 3D axes dimensions it is not possible to generate and effective titration of the drug effect over cell response through a diffusion gradient. These results demonstrate that the proportions of the well containing the hydrogel are of pivotal relevance to obtain a gradient of diffusion that is at the same time measurable, stable and capable of providing reliable information in connection to the titration of the drug's effect. In addition, and as illustrated in FIG. 16A, the use of multi-well standard plates filled with a liquid medium, wherein each well comprises different drug concentrations, fails to provide a gradient of diffusion that is at the same time measurable, stable and capable of providing reliable information in connection to the titration of the drug's effect. In this sense, it is important to note that titration of an immunosuppressant drug's effect by using serial dilutions in standard well plates as illustrated in FIG. 16A, fails to provide a result which may be consider equivalent to those obtained through the spontaneous gradient diffusion in hydrogels having the dimensions described in new claim 1. In this sense, the use of serial dilutions in standard wells is based on the use of a number of arbitrary concentrations values and/or serial dilutions ratios, which shall always involve a considerable loss of information due to the lack of intermediate concentrations that can be extremely relevant to the shaping of titration curves, consequently reducing the accuracy of the titration results, and second there is a limitation in the number of potential scanning points associated with standard plates that implies one reading point per well. On the contrary the approximation with channeled wells having the dimensions indicated in the claims (FIG. 17), generates a continuous gradient with an undetermined number of scanning points, considerably higher than those generated in standard well plates and only limited by the configuration of the fluorescence readers. Such scanning accuracy and sensibility, provided by the approach generated in the channeled wells described in the claims, are necessary to generate data with clinical utility for the detection of susceptibilities and resistances to different immunosuppressive drugs. As illustrated in the FIG. 23, by using the methodology described in the claims, we are able to screen for resistant or sensitive patients to specific immunosuppressant drugs. This is of pivotal importance in order to reduce the number or potential false positive and false negative results, thus leading to an improved clinical diagnostic tool.

Figure 14:
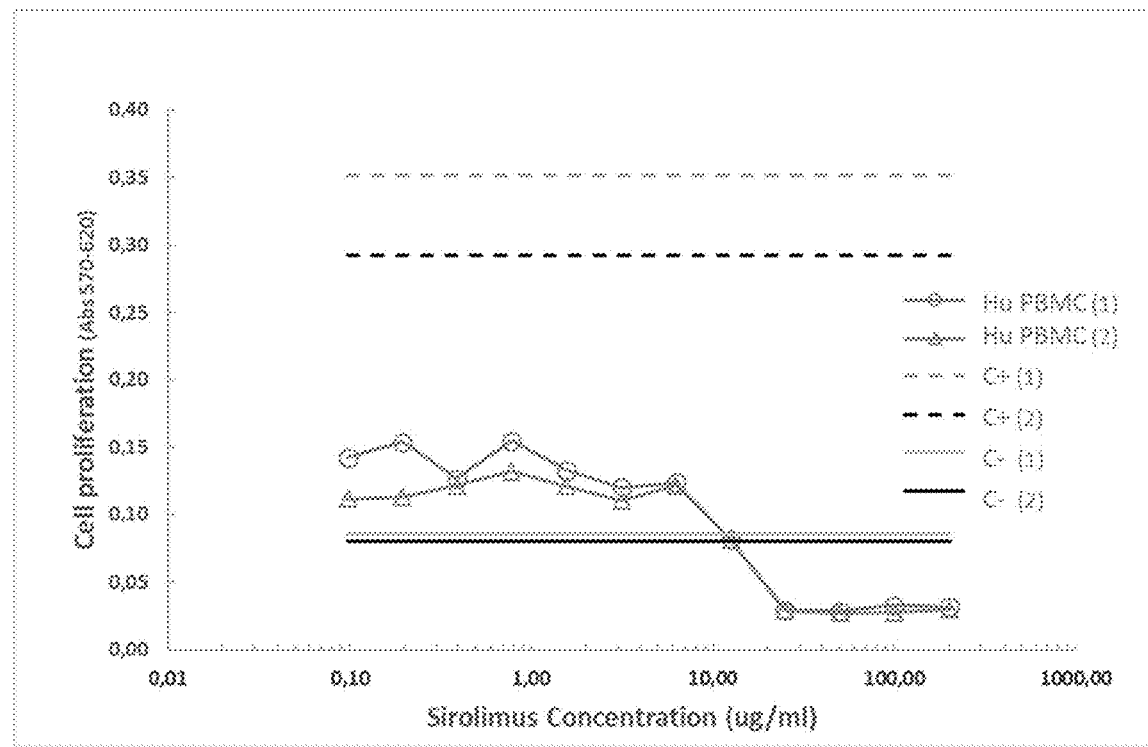
FIG. 14. Dose dependent effect of Sirolimus immunosupressant serial dilutions over activated human PBMCs from two different human volunteers (Hu PBMC 1 and 2). C+=positive control (PBMC stimulated with dynabeads) C-=negative control (unstimulated PBMC).
Figure 15:
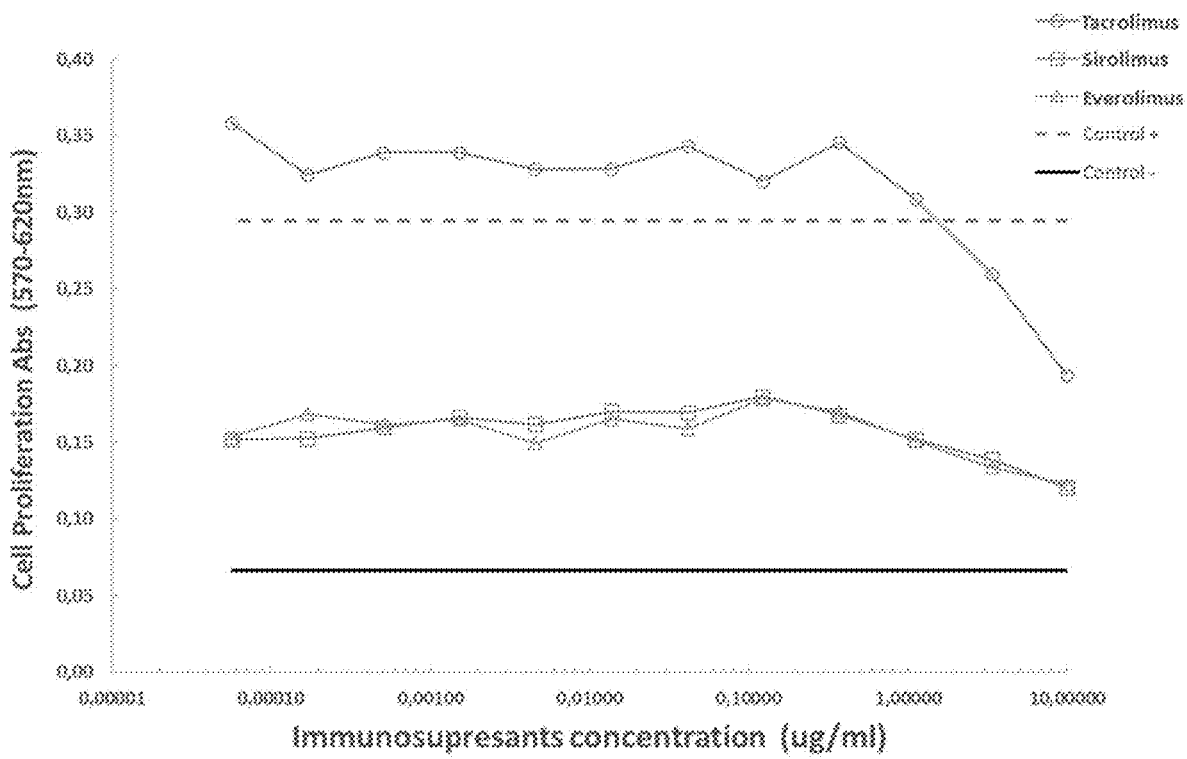
FIG. 15. Dose dependent effect of immunosupressants (Tacrolimus, Sirolimus, Everolimus) serial dilutions over activated human PBMCs over Human PBMCs.
Figure 17:
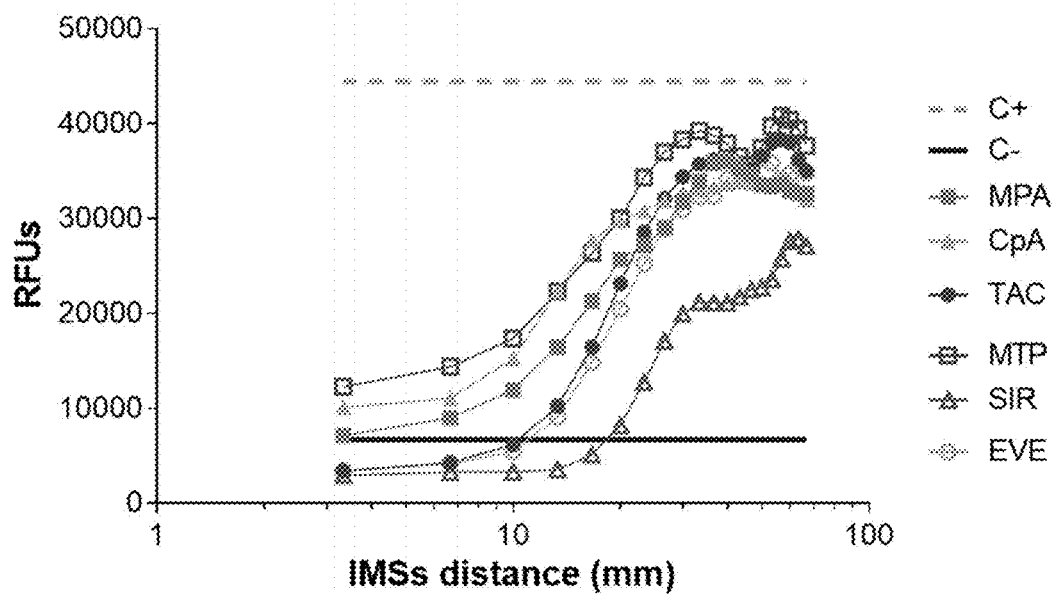
FIG. 17 Representation of the inhibitory gradient effect of different immunosuppressant drugs over two different PBMCs human donors (upper and lower graph) included in copolymer hydrogel collagen-methyl cellulose. C+: positive control (PBMC stimulated with dynabeads); C-: negative control (unstimulated PBMC); MPA=Mycophenolic Acid; CpA=Cyclosporine A; TAC: tacrolimus; MTP. Methyl Prednisolone SIR: Sirolimus; EVE=Everolimus.
Figure 17:
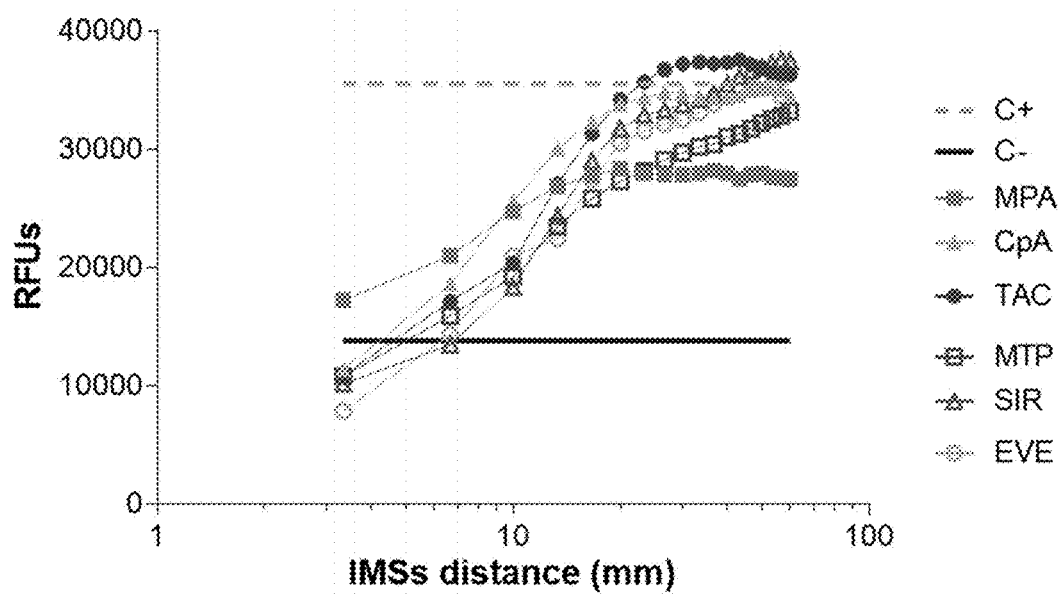

Therefore, only the titration of all immunosuppressants tested by using channeled wells characterized as in the claims, we were able to provide a measurable and stable drug gradient flux in the major axis of the described channeled well containing the human PBMCs embedded within the hydrogel, thus generating a quantifiable titration of the dose dependent effect of these drugs after diffusion based gradient generation, including mTOR inhibitors designed as IMS 5 and 6, as shown in FIG. 17. The fact that our system is capable of titrating any immunosuppressant drug including mTOR inhibitors is important, since in our experimental systems, by using standard wells, and in all the attempts to quantify the dose dependent inhibitory effect of mTOR signalling pathway inhibitors (immunosupressants: Sirolimus and Everolimus) over stimulated human PBMCs, we were not able to correctly quantify said dose dependent inhibitory effect. The reason was because at all the concentrations tested (even at femtomolar levels) there was at least some inhibitory level effect and because positive control of proliferation in the absence of immunosupressants was never reached. In additional experimental systems, by using standard 96 standard wells microplate serial dilutions of mTOR inhibitors: Sirolimus and Everolimus, as shown in FIGS. 14 and 15, were not able to generate effects over PBMCs proliferation/activation that ranged from the cells without stimuli (negative control reference, continuous line) to anti-CD3/CD28 dynabeads stimulated cells (positive control+discontinuous line). In this sense, at all concentration tested, even at femtomolar levels, human PBMCs did not recover proliferative capacity comparable with positive control level. Thereby, for mTOR inhibitors, titration of dose dependent effect over cell proliferation is not viable by using standard format wells, and therefore no quantifiable data could be obtained to titrate the drug effects by using standard wells.

It is thus clear, that in order to generate a concentration gradient by diffusion of the immunosuppressant as described in the claims, the use of non-circular wells defined as channeled wells or channels characterized by a dimensional proportion in which one of the spatial three axes (longitudinal axis) is at least 4 times longer than the length average of the two other axes, is consider essential.

In addition, and as indicated above, not only the use of non-circular wells is consider essential but also the selection of the correct type of hydrogel is essential to correctly practice the present invention. In this sense, hydrogel suitability requirements in the context of activated and inactivated PBMCs are defined as those compositions that generate a non-toxic environment able to sustain cell proliferation (adequate nutritional composition and stiffness), and absent of unspecific induction of PBMCs activation. In particular, only hydrogels compositions that allow an adequate signaling of positive and negative control, more precisely hydrogel compositions that do not negatively affect cell proliferation of immunologically activated PBMCs (positive control) nor do they generate an unspecific activation/proliferation of inactivated PBMCs (negative control), can be use in the context of the present invention.

In this sense, not all hydrogels available for 3D cell culture can be use in the context of the present invention. In this sense, if we were to use alginate hydrogels, and since these hydrogels polymerized in the presence of relevant concentrations of calcium, wherein calcium is one of the pivotal intracellular signalling element of cells response (including lymphocytes); a background effect would be created by said introduction of calcium (Chan G. et al. Acta Biomater. 2013 December; 9(12)), an effect clearly detrimental for carrying out a lymphocyte functional assay for testing inmunomodulators. Second, if the skilled person were to use Matrigel® hydrogels, and since these hydrogels include tumoral derived factors that interplay with the activation and immunoregulation of cells embedded within, the use of this hydrogel would negatively affect the results of the assay in the context of immune cells activation. Thirdly, as taught in example 2, percentages of collagen above 0.3% (gr/100 ml) are not compatible with the proposed assay.

The method of the present invention provides an experimental window (C+/C− ratio) that correlates with the patient's immunological state, being the hydrogel composition/characteristics, as illustrated above, one of the most relevant elements in this regard. In this context, the stiffness of a hydrogel is the result of the relative percentage of the presence of polymeric compound/s in the aqueous solution. Such stiffness must be within a range that provides enough consistency to maintain the stability of the immunosuppressant drug gradient and avoids spilling, but not higher than a stiffness level that inhibits cell growth due to an excessive mechanical stress or impedes its handling during the bioassay procedure.

In this sense, FIG. 24 represent differences in hydrogels allowance for activated PBMCs proliferation. In figure A, the different proliferation rate of same donor derived activated PBMCs is represented. In this case agarose 0.5% is clearly a better cell environment for proliferation than methyl cellulose-clonacell and bioglex peptides. Figure B clearly shows how Pluronic hydrogel (F-127) is toxic and inhibits the proliferation of activated PBMCs (C+) compared with the optimized hydrogel composition of the copolymer (methyl cellulose/collagen).

In addition, the non-specific activation of PBMCs is a relevant issue in the context of the immunological in vitro assays of the present invention. This is clearly reflected in FIG. 25, wherein the effect of collagen hydrogel at 0.3% and 0.5% is evaluated comparing positive and negative controls of PBMCs activation at two different time points. At early incubation time (24 h), collagen at 0.5% is able to induce a high and unspecific activation generating high levels of proliferation, measured as relative fluorescence; in both positive and negative controls. After 48 h of incubation, collagen at 0.3% allows the generation of an activation window, on the contrary 0.5% collagen induces a later inhibition of proliferation both in negative and positive control cells. Finally, but not less important, the stiffness of the hydrogel, apart from its effect on the viability of the cells, has a direct effect on the operability of the product associated with the execution of the cell bioassays. It has been proven that for each polymer there is an adequate concentration range to avoid excessive flow or rigidity after hydrogel polymerization. For some of the gels tested we have determined the following preferred operating range values (although other values and types of hydrogels are further detailed later-on in the present specification):

If the hydrogel is a polymeric based hydrogel comprising agarose, the concentration should be equal or below to 0.5% gr/100 ml;

If the hydrogel is a protein based hydrogel comprising collagen, the concentration should be below or equal to 0.3% gr/100 ml;

If the hydrogel comprises a total polymeric fraction which consists of methyl cellulose and collagen, the methyl cellulose content should be equal or below 4% gr/100 ml, more preferably below or equal to 2% gr/100 ml, and collagen content should be bellow or equal to 0.3% gr/100 ml.

It is thus clear, that in order to generate a concentration gradient by diffusion of the immunosuppressant as described in the claims, the use of a specific hydrogel composition as detailed above as well as the use of non-circular wells defined as channeled wells or channels characterized by a dimensional proportion in which one of the spatial three axes (longitudinal axis) is at least 4 times longer than the length average of the two other axes, are consider essential.

Lastly, immunosuppressive drug diffusion into the hydrogel must be the generated from a dry, concrete quantity deposited at the edge of a channeled well in a device or formulation capable of deliver the product into the hydrogel through a passive diffusion process. In this sense, in our experimental systems, by using standard liquid cell culture mediums with specific and individual concentrations per standard well, the hydrophobic compounds (the majority of immunosuppressant active compounds) require organic solvents (DMSO, Ethanol) that could generate toxicity, partial precipitation at high concentrations and in vitro bioavailability variations. In contrast, with standardized disks loaded with dry immunosuppressants there is a passive dilution process through diffusion from the disc over to the hydrogel once included on top of the hydrogel. In this case the inhibitory migration front, developed through the channeled well, generates more precise data, avoiding variations and wrong data interpretation due to solubility issues. Therefore, solubility is not an issue in the conditions described in the channeled wells of the present invention since diffusion is defined by immunosuppressant chemical characteristics (polarity, molecular weight, etc), hydrogel % and media composition, and all these parameters are more easily standardisable.

In summary, only by using the channeled wells, complying with the above mentioned technical features, we were able to provide a measurable and stable drug gradient flux in the major axis of the described channeled well containing the human PBMCs embedded within the hydrogel, thus generating a quantifiable titration of the dose dependent effect of these drugs after diffusion based gradient generation, including mTOR inhibitors designed as IMS 5 and 6, as shown in FIG. 17.

The reason for this is because spontaneous diffusion of a substance in a hydrogel depends on several parameters like solute characteristics (concentration, molecular size, solubility, polarity, etc), hydrogel network characteristics (pore size, chemical monomer structure, crosslink degree, mesh size, etc), temperature, pH, ions presence, etc. This substance diffusion (immunosupressants) generates a concentration gradient that exerts a dose dependent inhibitory effect over the hydrogel embedded cells' proliferation.

Diffusion occurs in water but a stable concentration gradient of a substance can only be measured in the absence or minimal presence of fluid alteration due to external forces. Hydrogels generate a molecular mesh that stabilizes the physical and mechanical properties of the fluid that contains the compound gradient in progress. In the case of the present invention, biological hydrogels made from different polymers are used to establish biomolecule gradients around cells in vitro. Introducing a known concentration of a compound (Immunosupressants) within the gel, the biomolecule diffuses randomly away from its source into the gel forming a concentration gradient over the embedded cells that evolves steadily in both, space and time scales when other affecting variables like solute and hydrogel characteristics and temperature are fixed and stable.

Figure 18:
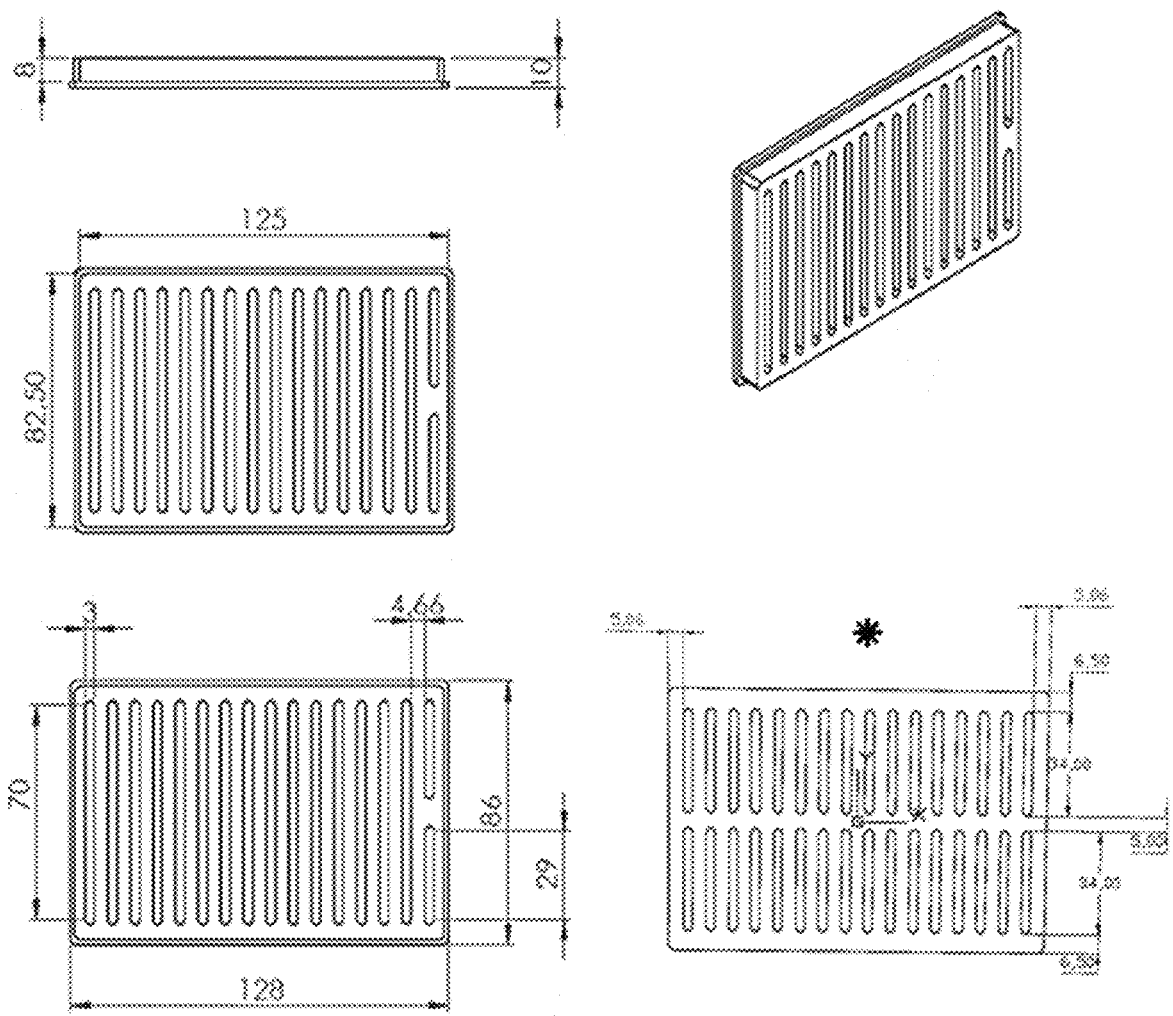
FIG. 18. Microplate graphical design representation example with different channels length size. All numbers refer to metric values of length, width and height of external and internal elements of the microplate, in millimetre units. Optional plate design with channels length of 34 mm.
Figure 19:
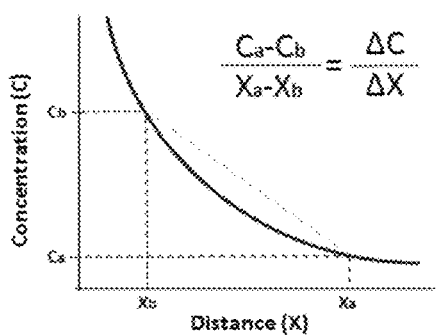
FIG. 19. Representation of diffusion evolution in a hydrogel evaluating a single space axis. Graphical representation of concentration differences (Ca, Cb) in two different spatial point (Xa, Xb) as a result of the solute diffusion in a hydrogel (A). Graphical representation of a diffusion gradient as the slope of curve representing a solute concentration variation in function of distance incrementation (B).
Figure 19:
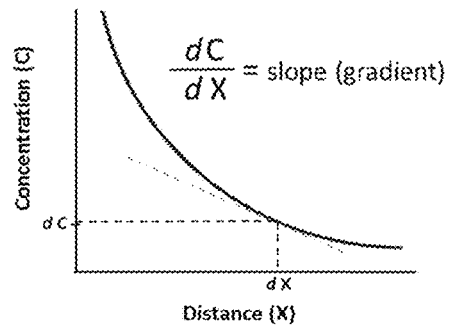

To take place such diffusion forming a concentration gradient, hydrogels must be included in longitudinal channels, where the longitudinal axis is X (X>>Y~Z) and wherein the gradient develops virtually in one dimension. In this simplified one dimension fick's first law scenario, the gradient is function of concentrations and distance between defined spatial points. The derivative of infinitely close spatial concentration variations (dC/dX) corresponds to the slope (FIG. 18). The gradient magnitude is a vector defined by the partial derivatives of axes system components (X, Y, Z). Moreover, when the distance increment ($\Delta X = Xa - Xb$) is low, the concentration differences between the corresponding spatial points is limited and consequently the gradient is reduced or undetectable in practice (FIG. 19-B). In reduced isometric 3D compartments (microplate small circular wells, 100-500 ul volume) the limited distance in the three-spatial axes generates a fast diffusion and very low gradient. In proper channels (narrow and long) where two of the three axes are significantly lower than the other, diffusion develops slowly and steadily enough along longitudinal axis (X) to allow a wide gradient to be properly quantify (FIG. 17).

All of these previous statements are not applicable to microfluidics.

Therefore, measurable diffusion gradient in hydrogels included in microplate devices requires a spatial distribution in the three spatial axes with at least one axis with a distance range of at least 4 times the average of the other two axes, defined as channeled wells or channels. There by, circular and equilateral squared wells microplates are definitely discarded from this definition. In this manner, longitudinal rectilinear, curvilinear or sinusoidal channels, or any combination of mentioned shapes, allow for a wide range concentration gradient capable of being generated thereby thus providing a dose dependent measurable effect over the cultured cells embedded within the hydrogel. In this description, longitudinal term is defined as the axis along the higher length direction of a figure, or body passing through its geometrical of gravity centre, rectilinear is defined as a shape bounded by parallel straight lines, curvilinear is defined as a shape consisting of or bounded by curved lines (Lack of straightness) and sinusoidal is defined as a shape like, or varying according to a sine curve or sine wave (repetitive oscillation).

Therefore, in order to generate a quantifiable titration of the dose dependent effect of immunosuppressant drugs, including mTOR inhibitors, after diffusion based gradient generation in a hydrogel, it is mandatory for the method of the present invention to use a channeled well or microplate characterized by dimensional proportions in which one of the spatial three axes (longitudinal axis) is at least 4 times, preferably at least 5 times, preferably at least 6 times, more preferably at least 7 times, more preferably at least 8 times, more preferably at least 15 times, longer than the length average of the two other axes. An example of a microplate useful in the present invention is shown in FIG. 18 enclosed herein; in particular, a plate of the following dimensions: 127.76±0.25 mm length, 85.48±0.25 mm width and 10-15 mm height. Channels included in such plate are preferably between 20 to 70 mm length, from 1 to 4 mm width and 7 to 10 mm height, such channels should be able to contain a hydrogel volume per channel from 40 to 2.800 µl. It is important to note that channeled wells or microplates useful in the present invention excludes channeled wells or microplates useful in microfluidics, that is defined by devices in the well volume range of 10 microliter (µL) to femtolitre (fL) (Chem. Soc. Rev., 2010, 39, 1153-1182), in this sense, the channeled well or microplates useful in the present invention must be able to contain a hydrogel volume per well of at least 40 µl, preferably from 40 µl to 2.800 µl.

Preferably, the microplates useful in the present invention comprise a multiplicity of channels for holding samples to be assayed by light emissions, transmission or absorbance, said plate comprising an upper plate forming the side walls of the sample wells, channels or reservoirs, said side walls being polymeric opaque plastic so that light cannot be transmitted between adjacent channels through said side walls, a lower fused and sealed sheet forming the bottom walls of the sample wells, said bottom walls being transparent to allow the transmission of light there through, said lower plate being polymeric plastic part compatible with cell culture, an upper plate lid being a single unitary transparent plastic part with compatible dimensions to fit the described microplate.

Microplates useful in the present invention can be made by any materials with no ability to affect the viability or activation of cultured cells, including but not restricted to polystyrene, polypropylene, polycarbonate or cyclic olefin copolymer derivatives.

To the best of our knowledge, this is the first time that the above mentioned channeled wells are used in a method to quantitatively measure the response of a patient to an immune-modulator drug that will aid clinicians in the determination of the optimal combination/posology of immunosuppressant/immune-modulator drugs.

Based on all of the above criteria, a first aspect of the invention refers to a method to quantitatively measure the response of a patient to an immune-modulator drug, the method comprising the following steps:
a. Activating peripheral blood mononuclear cells (PBMCs), total leukocytes or specific sub-populations of PBMCs such as T-lymphocytes, regulatory T cells (Tregs), NK (Natural Killer cells), macrophages or B-lymphocytes, obtained from a biological sample selected from the list consisting of blood or blood cellular derivatives of the patient, though incubation with a lymphocyte activation compound selected from the list consisting of: agonistic antibodies anti CD3 (TCR) and CD28, ionomycin and PMA (phorbol myristate acetate), lectins, superantigens, Lipopolysaccharides (LPS), antigen determinants or epitopes and through a Mix Lymphocyte Reaction;
b. Obtaining a hydrogel which in turn comprises the activated PBMCs, total leukocytes or specific sub-populations of PBMCs, embedded within the hydrogel wherein the hydrogel is located in a support or microplate comprising channeled wells or channels characterized by having a dimensional proportions in which one of the spatial three axes (longitudinal axis) is at least 4 times, preferably at least 5 times, preferably at least 6 times, more preferably at least 7 times, more preferably at least 8 times, more preferably at least 15 times, longer than the length average of the two other axes, so that the hydrogel is capable of providing a measurable and stable drug gradient flux in the major axis of described channeled wells, wherein the channeled wells contain a hydrogel volume per channel of at least 40 l and wherein the channeled well should be covered completely by the hydrogel in its longitudinal axis and should covered at least a 30% of the channeled well height;
c. Contacting the hydrogel of step b) with one or more immune-modulator drugs;
d. Adding a solution of a compound capable of revealing an inhibitory zone around the site of contact of the immunosuppressant drug with the hydrogel; and
e. Obtaining the quantification of the immune-modulator drug gradient formed, preferably by image acquisition or signal quantification (absorbance, fluorescence or luminescence);

wherein the hydrogel is a viscoelastic solid-like material comprised of an elastic cross-linked network and water, wherein water is the major component; wherein molecular entanglements and/or secondary forces such as ionic, H-bonding or hydrophobic forces play the main role in forming the elastic cross-linked network; and wherein the hydrogel is selected from the list consisting of protein based hydrogels, peptide based hydrogels and polymeric based hydrogels.

It is noted that the hydrogel, as already explained above, must comply with certain characteristics that includes biocompatibility with cell culture, toxicity-free, adequate and controllable stiffness over assay running time and consistent operability with the requirement of each assay step. In this sense, hydrogel suitability requirements in the context of activated and inactivated PBMCs are defined as those compositions that generate a non-toxic environment able to sustain cell proliferation (adequate nutritional composition and stiffness), and absent of unspecific induction of PBMCs activation. In particular, only hydrogels compositions that allow an adequate signalling of positive and negative control, more precisely hydrogel compositions that do not negatively affect cell proliferation of immunologically activated PBMCs (positive control) nor do they generate an unspecific activation/proliferation of inactivated PBMCs (negative control), can be use in the context of the present invention.

It is further noted, that step c) of the above mentioned methodology results in the formation of an immune-modulator drug gradient in the hydrogel. Such gradient requires a diffusion of the immunosuppressant in the hydrogel located in a support or microplate comprising channeled wells characterized as above, capable of providing a drug measurable and stable gradients flux in the major axis of described channeled wells or channels. Diffusion is defined as the net movement of particles from a region of high concentration to a region of low concentration following the concentration gradient (Fick's first law). In this case, concentration gradient is a change in values of quantity of two variables: concentration over distance. Thereby, gradient diffusion in hydrogels could be defined as the rate of change of a substance concentration with respect to distance of diffusion from an initial spatial point As shown in example 3, liquid media dilution methods in microplate format in the context of specific proliferative inhibition of activated PBMCs, require between 3 to 5 days of culture to detect response variations in activated human lymphocytes proliferation. In contrast, obtained results with the hydrogel diffusion assay (semisolid formats) as described in the first aspect of the invention, allows interpretation of immunosuppressant's activity in 2-3 days. In particular, the semisolid format after 24-48 hours of stimulation and during the following 24 hours, detects differences between negative and positive controls, and inhibitory front could be visualized or detected. Also the number of testable compounds number was higher in semisolid formats. Moreover, while microplate tittering requires manual or automated serial dilutions with at least triplicates to have acceptable statistical power and detect edge effect during the long period assay (medium evaporation effect), hydrogel format generated a homogeneous evaporation rate.

Furthermore, PBMCs (lymphocytes) in vitro growth requires stimulation, close cell contact (96 well microplates U bottom) and several days in liquid cell culture medium. However, unexpectedly, after stimulation, PBMCs seeded and scattered in a 3D hydrogel grow, as the one described in the first aspect of the invention, maintain a good viability that could be measure at shorter times comparing with similar condition in liquid culture medium. In addition, based on the common general knowledge we expected the requirement of lymphoblast colonies formation and growth (that require several days) to measure the effect of immunosuppressant diffusing from discs. But the results showed that there is no need for real proliferation or colony formation in 3D hydrogels format to measure cell activity and inhibitory halos, which constitutes a further improvement of the methodology described in the first aspect of the invention.

The advantages of the method described in the first aspect of the invention are thus the test simplicity, the provision of categorical results easily interpreted by all clinicians, and flexibility in potential selection of immunoregulators loaded disks for testing. It is the least costly of all susceptibility methods. Also, with standardized disks, solubility is not an issue since diffusion is defined by immunosuppressant polarity and MW (molecular weight), hydrogel % and media composition, and all these parameters are easily standardisable. In contrast, in plates with liquid medium, hydrophobic compounds (almost all immunosuppressant active compounds) require organic solvents (DMSO, Ethanol) that could generate toxicity, partial precipitation at high concentrations and in vitro bioavailability variations. Yet, the semisolid media performs a passive dilution process through diffusion from the disc over the hydrogel and homogeneous evaporation rate, so inhibitory halos generate more reliable information in shorter assay time periods and avoid variations and wrong data interpretation due to solubility issues.

Considering the solubility profile of the leading immunosuppressant drugs currently in use for different chronic inflammation conditions (Prednisone, Methylprednisolone Hemisuccinate Na, Prednisolone, Mycophenolic acid, Azathioprine, Cyclosporine A, Tacrolimus, Sirolimus, Everolimus) the majority present very poor water solubility. It is important to notice that only active metabolic derivatives should be tested in in vitro assays, since it is the active pharmaceutical ingredient the one that exerts the biological activity. In this context, only Mycophenolic acid presents a good aqueous solubility. In addition, compound solubility in buffers, ethanol and dimethyl sulfoxide (DMSO) has emerged as important issues in drug research. Many active compounds have low solubility but are potentially valuable as leads and research analysis. Unfortunately, low solubility affects microplate bioassays by causing underestimation activity, reduced sensibility, variable data, and inaccurate in vitro activity testing. Moreover, dilutions could mask toxicity of immunosuppressant active pharmaceutical ingredients and modify its physical structure. Strategies for optimizing microplate bioassays requires considering solubility in HTS-library design; early screening for solubility; improving storage and handling of DMSO stocks; optimizing dilution protocols; and ensuring that low-solubility compounds are fully solubilized in bioassays. In contrast, the hydrogel semisolid diffusion method of the first aspect of the invention solves many of described issues related with the solubility challenge. Lastly, microplate format requires some extra-manipulation steps that increase the possibility of errors and are not desirable for automated assays (Cell Viability Assays Terry L Riss, PhD* Promega Corporation).

Therefore, the assay or method of the first aspect of the invention generates a simplified quantitative tool able to measure the cellular response of a subject, preferably a human subject, to a panel of immunosuppressant or immunomodulators compounds or drugs. Results interpretation depends on relative response and validation among healthy and different patients' profiles. Once stablished the drug discs load and inhibitory halos range of reference, clinicians will obtain data of relative efficacy of different drugs in order to select the drug o multi-therapy combination and range of doses that could better treat the patient's pathology, generating the better immunosuppressive effect with lower secondary and toxic effects. In addition, this assay system could generate complementary information about patient's lymphocytes responsiveness in the presence or absence of stimulation.

In a preferred embodiment of the first aspect of the invention the activation step a) is performed by using agonistic antibodies anti CD3 (TCR) and CD28, preferably magnetic polymer beads coated with Human T-activator CD3/CD28 agonistic antibodies.

In another preferred embodiment of the first aspect of the invention or of any of its preferred embodiments, the hydrogel is formed through covalent or non-covalent crosslinking of polymer chains, preferably non-covalent crosslink (physical hydrogels), wherein the total polymeric fraction represents less than 5% gr/100 ml, preferably less than 3% gr/100 ml, and is selected from the group consisting of collagen, fibrin, agarose, auto-assembling polypeptides, alginate, cellulose derivatives, hyaluronic acid, polyethylene glycol, chitosan or its combinations. Preferably, the total polymeric fraction consists of agarose, methylcellulose or collagen, wherein agarose content is preferably equal or below 1% gr/100 ml, more preferably below or equal to 0.5% gr/100 ml, and collagen content is preferably below or equal to 0.3% gr/100 ml; and methylcellulose at a concentration of about 1.4% wherein the final polymeric component is 1.65% approximately (weight in grams per 100 ml of hydrogel)

Thermogels that remains liquid at low temperatures and became gels at higher temperatures are specially preferred in the present invention due to their characteristics of high compatibility with cell culture and viable standardization of handling and potential high reproducibility of results and compound conditions. Agarose is especially difficult to handle because its physicochemical properties under temperature changes are the opposite to these explained.

In particular, a hydrogel comprising a mixture of collagen and methylcellulose, preferably of bovine collagen and methylcellulose, more preferably of bovine collagen at a concentration of about 0.15% and Methylcellulose at a concentration of about 1.4% wherein the final polymeric component is 1.65% approximately (weight in grams per 100 ml of hydrogel), is particularly preferred, as physico-chemical properties adjust to targeted ones (remains liquid at low temperatures and became gel at higher temperatures).

In another preferred embodiment, the hydrogel comprises methyl cellulose. Preferably a hydrogel wherein the total polymeric fraction consists of methyl cellulose and/or collagen, and wherein methyl cellulose content is equal or below 4% (gr/100 ml of hydrogel), preferably below or equal to 2% (gr/100 ml of hydrogel), and collagen content is below 0.5% (gr/100 ml of hydrogel), preferably bellow or equal to 0.3% (gr/100 ml of hydrogel).

In another preferred embodiment, the hydrogel comprises a total polymeric fraction which consists of methyl cellulose and/or collagen, wherein methyl cellulose content is preferably equal or below 4% gr/100 ml, more preferably below or equal to 2% gr/100 ml, and collagen content is preferably below 0.5% gr/100 ml, more preferably bellow or equal to 0.3% gr/100 ml.

In another preferred embodiment of the first aspect of the invention or of any of its preferred embodiments, the hydrogel contains more than 95% of aqueous phase, preferably more than 97%, preferably being this aqueous phase a cell culture medium, preferably minimal mediums without animal serum, phenol red or antibiotics.

In another preferred embodiment of the first aspect of the invention or of any of its preferred embodiments, the hydrogel is a protein based hydrogel comprising collagen, preferably in a concentration below or equal to 0.3% gr/100 ml, obtained or obtainable by using a cell culture collagen solution and mixing said solution in step b) with the activated cells of step a), wherein once mixed the solution is warmed at a temperature of about 37° C. for 30 to 150 minutes, preferably for about 90 minutes, until formation of the gel.

In another preferred embodiment of the first aspect of the invention or of any of its preferred embodiments, the hydrogel is a polymeric based hydrogel comprising agarose, preferably in a concentration equal or below 1% gr/100 ml, more preferably below or equal to 0.5% gr/100 ml, obtained or obtainable by using a cell culture agarose solution at a temperature of about 37° C. and mixing said solution in step b) with the activated cells of step a), wherein once mixed the solution is cool to a temperature of about 25° C. for 10 to 15 minutes until formation of the gel and then warmed again to a temperature of about 37° C.

In another preferred embodiment of the first aspect of the invention or of any of its preferred embodiments, the solution of step d) is a resazurin solution. It is noted that other options to reveal cell activity are available and known to the skilled person and could be compatible with the hydrogel assay to define inhibitory zones around immunosuppressant discs.

In another preferred embodiment of the first aspect of the invention or of any of its preferred embodiments, the method to quantitatively measure the response of a patient to an immune-modulator drug gradient is aim at preventing and treating chronic inflammatory conditions such as progressive multiple sclerosis, rheumatoid arthritis, transplant rejection, and many others.

A second aspect of the invention refers to the in vitro use of a hydrogel which in turn comprises activated PBMCs, total leukocytes or specific sub-populations of PBMCs, embedded within the hydrogel for quantitatively measure the response of a patient to an immune-modulator drug. Preferably, for quantitatively measure the response of a patient to an immune-modulator drug to assist the physician take the decision of what drugs/combinations, regimens, dosages . . . should be used to treat a subject, in particular a human patient, preferably suffering from a chronic inflammatory condition such as progressive multiple sclerosis, rheumatoid arthritis or transplant rejection.

A third aspect of the invention refers to a kit or device suitable for quantitatively measure the response of a patient to an immune-modulator drug, which comprises:
   a. A support with one or more channels capable of comprising a hydrogel which in turn comprises activated PBMCs, total leukocytes or specific sub-populations of PBMCs, embedded within the hydrogel. It is important to note that such support or microplate comprises channeled wells or channels characterized by having a dimensional proportions in which one of the spatial three axes (longitudinal axis) is at least 4 times, preferably at least 5 times, preferably at least 6 times, more preferably at least 7 times, more preferably at least 8 times, more preferably at least 15 times, longer than the length average of the two other axes, so that the hydrogel is capable of providing a measurable and stable drug gradient flux in the major axis of described channeled wells, wherein the channeled wells contain a hydrogel volume per channel of at least 40 µl and wherein the channeled well should be covered completely by the hydrogel in its longitudinal axis and should covered at least a 30% of the channeled well height;

In a preferred embodiment of the third aspect of the invention, such kit or device further comprises one or more of the following elements:
   a. a lymphocyte activation compound selected from the list consisting of: agonistic antibodies anti CD3 (TCR) and CD28, ionomycin and PMA (phorbol myristate acetate), lectins, super-antigens, Lipopolysaccharides (LPS), antigen determinants or epitopes;
   b. A cell culture solution capable of providing a hydrogel, wherein the hydrogel is a viscoelastic solid-like material comprised of an elastic cross-linked network and water, wherein water is the major component; wherein molecular entanglements and/or secondary forces such as ionic, H-bonding or hydrophobic forces play the main role in forming the elastic cross-linked network; and wherein the hydrogel is selected from the list consisting of protein based hydrogels, peptide based hydrogels and polymeric based hydrogels; and a c. Compound capable of revealing an immune-modulator drug gradient effect, preferably by image acquisition or signal quantification.

In a preferred embodiment of the third aspect of the invention, the kit further comprises a physical support for contacting the hydrogel with one or more immune-modulator drugs such as a disc, a cylinder or a strip having a concentration of the immune-modulator drug, wherein said physical support is made of any porous material capable of releasing the immune-modulator compound once in contact with the hydrogel.

In another preferred embodiment of the third aspect of the invention or of any of its preferred embodiments, the kit further comprises immune-modulator drugs such as an immunosuppressant (glucocorticoids, calcineurin inhibitors, mTor inhibitors, DNA synthesis inhibitors or others).

In another preferred embodiment of the third aspect of the invention or of any of its preferred embodiments, the lymphocyte activation compound are antibodies anti CD3 (TCR) and CD28, preferably magnetic polymer beads coated with Human T-activator CD3/CD28 agonistic antibodies.

In another preferred embodiment of the third aspect of the invention or of any of its preferred embodiments, the compound capable of quantifying an immune-modulator drug gradient is a resazurin solution.

In yet another preferred embodiment of the third aspect of the invention or of any of its preferred embodiments, the hydrogel is a copolymer of protein based hydrogel and cellulose derivatives comprising collagen and methyl cellulose, preferably collagen in a concentration below 0.5% (gr/100 ml of hydrogel), more preferably bellow or equal to 0.3% (gr/100 ml of hydrogel), and methylcellulose at a concentration of about 1.4% wherein the final polymeric component is 1.65% approximately (weight in grams per 100 ml of hydrogel), obtained or obtainable by using a cell culture collagen solution and methylcellulose solution, mixing said solution in step b) with the activated cells of step a), wherein once mixed the solution is warmed at a temperature of about 37° C. for 30 to 150 minutes, preferably for about 90 minutes, until formation of the gel.

A fourth aspect of the invention refers to an in vitro use of the kit as defined in the third aspect of the invention or in any of its preferred embodiments, for quantitatively measure the response of a patient to an immune-modulator drug gradient. Preferably, for quantitatively measure the response of a patient to an immune-modulator drug gradient to to assist the physician take the decision of what drugs/combinations, regimens, dosages should be used to treat a subject, in particular a human patient, preferably suffering from a chronic inflammatory condition such as progressive multiple sclerosis, Rheumatoid Arthritis or transplant rejection. A non-limiting example of a chronic inflammatory condition for which the kit of the invention is useful would be for organ transplantation such as kidney transplantation before End-stage kidney disease (ESKD).

End-stage kidney disease (ESKD) is the last stage of a chronic kidney disease, which if not addressed leads to premature death and, although it can be addressed by dialysis, kidney transplantation is the preferred treatment due to better survival rates, improved quality of life and cost efficiency. ESKD can be clinical addressed either by dialysis or by kidney transplant. Because of better survival rates (>80%), improved quality of life and cost efficiency for the health systems (average monthly savings of €3.800 after transplantation), kidney transplantation is by far the preferred approach. However, clinical management of transplanted patients entails several challenges as explained below.

The most important challenge is to achieve the long-term survival of the transplanted organ (also known as graft or allograft). Graft survival depends on the ability of the recipient of not rejecting the "foreign organ". Rejection is a naturally occurring process triggered by a biological response of the immune system, which main function in the body is to defend it against infectious organisms and other invaders. As such, the immune system is prepared to reject a "foreign organ", something that is nowadays prevented by prescribing immunosuppressive therapies (drugs that suppress/reduce the effectiveness of the immune system) to the patients for their whole life. However, although immunosuppressive therapies have represented a huge step forward in organ transplantation, their use still entails important problems. On one side, suppressing the immune system implies severe side effects like opportunistic infections, cancer and other severe pathologies. On the other side, even under immunosuppressive therapies, about 50% of transplanted kidneys are lost during the first 10 years and this is because of an immune response usually described as chronic rejection. Organ rejection is the natural outcome after a kidney transplant. Rejection occurs as a result of humoral and cell-mediated responses by the recipient to specific antigens present in the donor tissue. These antigens are known as major histocompatibility complex (MHC) molecules or human leukocyte antigen (HLA) complex in humans. The HLA complex is a group of proteins in the cell membranes, which are expressed by the HLA system (genetic code) and it is unique for each person, except in monozygotic (identical) twins. Therefore, the HLA complex can be regarded as a "unique identification code". Whenever a donor organ is introduced into the recipient body, the immune system recognises the HLA complex of the new organ cells as a "foreigner" and immediately initiates the rejection response. Immediate/short term rejection is known as acute rejection and it has been almost totally addressed nowadays by the use of immunosuppressant medications.

Immunosuppressant therapy is initiated before the surgical process. At this moment, immunosuppressant drugs are administered at very high doses, as to suppress the patient immune system during the first hours/days after transplantation. Then, immunosuppressant therapy is gradually reduced until certain doses for reduction of immune system strength and maintained at these administration levels during the whole patient life. However, this strategy is not effective against chronic kidney rejection, which occurs in a 50% of cases in the next 10 years following transplantation (of which 7-16% within the first year). Chronic rejection is currently the major challenge in renal replacement therapy.

Therefore, a major challenge in kidney transplantation deal with finding the most effective immunosuppressant treatment scheme for each patient Patients undergoing a kidney transplant can show 3 different main immune response profiles in the long term (~10 years after transplantation): classic response of rejection controlled (40%), tolerance to the transplanted organ that allows for treatment down-escalation (10%) and chronic rejection (50%), understood as late outbreaks of rejection. For the 40% of patients with a classical response, immunosuppressive side effects could be reduced by adjusting the treatment to the actual patient needs. For the 50% of patients, whose outcome is chronic rejection, this could be prevented by the early adjustment (increase/change) of immunosuppressive therapy. For the 10% of patients showing an operational tolerance, immunosuppressive drugs could be gradually reduced or withdrawn without compromising graft survival. However, all these solutions cannot be currently implemented in the clinical routine because of the lack of effective means for monitoring allograft function and rational based approaches towards selection of the optimal immunosuppressive therapy.

In this sense, the methodology as well as the kit described in the present invention are particularly useful to assist the physician take the decision of what drugs/combinations, regimens and/or dosages, should be used to treat a patient which has had a kidney transplantation to prevent organ rejection. In fact, such methodology would be of great use in this clinical context, because there is no way apart from clinical guidelines and trial/error to take the decision of what immunosuppression scheme to be used after kidney transplantation. Furthermore, there is no system to monitor the evolution of the "sensitivity" of the cells of the immune system to these treatments, as is currently performed (for example) with antibiotics for the treatment of long lasting infections, in which sensitivity of target microorganisms to antibiotics is monitored with time and treatment modified accordingly.

EXAMPLES

Materials and Methods.
Peripheral Immune Blood Cell Isolation

After human blood collection by venipuction, separation of immune cells from whole blood sample could be asses by lysis of erythrocytes, isolating of mononuclear cells (PBMC) by density gradient separation, and assorting non-flow sorting methods, such as magnetic bead separations, for enriching specific cell populations, including monocytes, T lymphocytes, B lymphocytes, neutrophils, etc. Initially a whole blood sample or a fraction obtained as described above, could be freshly use for further phenotyping or in vitro assays or frozen immediately for further studies after appropriate thawing method.

PBMCs Stimulation

PBMC T-Cells were activated though incubation with Dynabeads Human T-activator CD3/CD28 agonistic antibodies (Thermo Fisher, cat #111.32D) using a ratio 1:2 (dynabeads:PBMC) in a cell culture bottle. PBMC in the absence of dynabeads were also cultured as negative control of stimulation.

However, other type of lymphocytes activation compounds should be considered such as:

a. Lonomycin+PMA (Phorbol Myristate Acetate):
Ionomycin is a calcium ionophore derived from bacteria (*Streptomyces conglobatus*), that increases intracellular calcium levels (Ca2+). PMA is a phorbol ester that induces a specific activation of PKC (protein kinase C) and thereof the NF-κB pathway (physiological response to TNF, LPS, MHC-TCR, BCR y growth factors receptors). Both compounds stimulate all type of cells and in PBMCs induce several cytokines production including IFN-g, IL-2, IL-4 and perforins.

b. Lectins (Con A/PHA/PWM):
Vegetable derived proteins (leguminous seeds), with high affinity to carbohydrates (glycoproteins and glycolipids). These proteins induce proliferation of T cells through unspecific membrane receptors agglutination, reproducing effects of type 1 and 2 immunological stimulation. Con A: Concanavalin A, PHA: phytohemagglutinin, PWM: pokeweed mitogen c. Superantigens:
Virus and bacteria derived proteins that induce unspecific binding of MHC-TCR inducing polyclonal activation of Lymphocytes and massive cytokines release. These proteins are able to activate 25% of lymphocytes in the absent of antigen determinants, some of them can specifically stimulate B lymphocytes.

d. Lipopolysaccharide (LPS):
Gram negative bacteria wall derivatives (endotoxins) that bind the CD14/TLR4/MD2 membrane complex of different cell types (monocytes, macrophages, dendritic cells, B cells) inducing proinflammatory cytokines, NO and eicosanoids. Though monocytes LPS induces IL-10 release and Treg activation (immunosuppressant profile).

e. Antigen Determinant or Epitope (Peptides):
Peptide sequences presented at the MHC (type II) of Antigen presenting cells (macrophage, dendritic cells and B lymphocytes) to the TCR of T lymphocytes. These peptides induce antigen specific activation through immunological signal type 1. This stimulation is limited, immunological memory component dependent and use to required secondary stimulation elements (IL-2) to generate potent proliferative responses.

f. Mix Lymphocyte Reaction (MLR):
Proliferative response induced by in vitro coculture of leucocytes from different donors or species. T cells from one donor react to MHC expressed antigens of other. One donor cells population use to be treated with radiation or Mitomycin C to block cell proliferation.

Hydrogels Preparation Procedures:
Methylcelullose: Clonacell™ (Stemcell technologies) methylcellulose solution was warmed in a water bath at 37° C. for 1 h, then 5 ml of PBS-10× (Biosolve) was added to 45 ml clonacell solution, finally 45 ml of X-VIVO (Lonza) complete methylcellulose solution. Cells were added in X-VIVO with a volume ratio of 1:20 with the previously prepared methylcellulose solution.

Collagens: collagen hydrogels were prepared with Pure-Col® EZ Gel solution 0.5% (Advance Biomatrix) in ice till use, to a final desired % diluted in X.-VIVO (Lonza). After cell addition and plate distribution, gelation requires 90 minutes.

Methylcelullose and collagen copolymer hydrogel were prepared mixing at 4° C., 70% in volume of previously prepared methylcellulose solution Methylcelullose: Clonacell™ (Stemcell technologies) and 30% in volume of Pure-Col® EZ Gel solution 0.5% (Advance Biomatrix) for a final hydrogel composition of collagen 0.15%. After cell addition and plate distribution, gelation at 37° C. requires between 5-30 minutes.

Agarose: agarose hydrogels were prepared with 4% agarose gel (Gibco) warmed in water bath to 70-80° C. during 10-15 minutes and then stored in a water bath at 37° C. till use. to a final desired % diluted in X.-VIVO (Lonza). Gelation takes place in seconds-minutes in a process that is time, temperature and agarose % dependent.

Autoassembling peptides: peptide hydrogel was prepared with biogelx peptide gel powder (Biogelx) 22 mg in 5 ml of sterile ultrapure water and store at 4° C. After addition of cells and plate distribution, after 90 minutes at 37° C. and 5% of $CO_2$, X-VIVO medium was added to wells and replaced after additional 3 hours.

Immunosuppressant Discs
Paper discs of 6 mm diameter discs were used as immunosuppressant delivery units. Discs were obtained from manual drill of Whatman™, 3 mm CHR chromatography paper sheet or using ready to use commercial paper disc (DDbiolab). Discs were sterilized by autoclave. Immunosupressant drugs (Sigma Aldrich) was dissolved in pure ethanol (Sigma Aldrich) at 20 mg/ml and stored as stock solution at −20° C. till use. Disc were loaded in sterile hood with 10-15 ul of ethanol containing different amounts of immunosuppressant drugs, ranging between 0.1 to 200 ug per disc. After ethanol evaporation (1 hour at 37° C. or 3 hours at RT) discs were placed in the centre (circular wells) or edge (channeled wells) of PBMCs containing hydrogels, 1 to 6 hours after hydrogel-cells addition to assure adequate gelation process.

Resazurin Addition

Resazurin solution (Presto Blue, Thermo Fisher) was added a different time periods in a volume ratio of 1:10 respect final volumen (hydrogel volume and presto blue+ X-VIVO).

Resazurin mechanism of action: Resazurin (7-Hydroxy-3H-phenoxazin-3-one 10-oxide) is a blue dye, itself weakly fluorescent until it is irreversibly reduced to the pink colored and highly red fluorescent. It is used as an oxidation-reduction indicator in cell viability assays for bacteria and mammalian cells, and for measuring aerobic respiration and exchange with the hyporheic zone in streams. Usually it is available commercially as the sodium salt.

Resazurin solution has one of the highest values known of Kreft's index. This means that it has a large change in perceived color (resolution) when the thickness or concentration of observed sample increases or decreases.

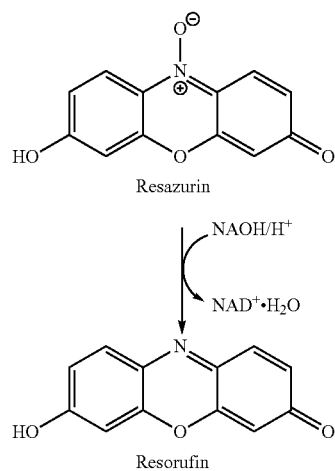

Resazurin is effectively reduced in mitochondria, making it useful also to assess mitochondrial metabolic activity. Usually, in the presence of NADPH dehydrogenase or NADH dehydrogenase as the enzyme, NADPH or NADH is the reductant that converts resazurin to resorufin. Hence the resazurin/diaphorase/NADPH system can be used to detect NADH, NADPH, or diaphorase level, and any biochemical or enzyme activity that is involved in a biochemical reaction generating NADH or NADPH. Other options to reveal cell activity are available and could be compatible with the hydrogel assay to define inhibitory zones around immunosuppressant discs.

Image Acquisition—Halos Quantification

Resazurin (blue) transition to resofurin (pink) was monitored with the naked eye or checked after overnight incubation depending on assay design. Reaction was stopped with 4° C. incubation. Results were collected through images acquisition with visible light (Sanyo camera S1070 und E1075), ultraviolet light (UVltec Geldoc Gel Light Imaging System) and fluorescence microplate multyreader (PHERAstar@ FSX Multimode Microplate Reader from BMG LABTECH or Spark® 10M Tecan.). Inhibitory gradients halos or fronts induced by discs loaded with immunosuppressants were quantified with ImageJ software in a semi-automated process or Spark control v1.2.25 software.

Example 1. Disc Diffusion Assay in Semisolid Media (Agarose 0.5% and Collagen 0.3% Hydrogels)

Agarose and collagen polymeric hydrogels were prepared from concentrated stock (4% and 0.5% gr/100 ml respectively) and diluted in cell culture medium to a final percentage of 0.5 and 0.3% gr/100 ml respectively. Agarose stock requires previous melting at 70° C. and collagen stock requires manipulation at 4° C. till use to avoid premature gelation. Immune cells, previously isolated and counted, were immediately added and mix with the hydrogel solution at a concentration in the range of 5,00,000 cells/ml, generating homogeneous 3D cells dispersion. Both solutions became semisolid in a period of time that ranged from 30 to 90 minutes depending on temperature (RT or 37° C.) and polymer percentage. After gelation, discs with different Cyclosporine A contents were place in the centre of the wells over the hydrogel surface. After 24 hours of incubation at 37° C. and 0.5% of $CO_2$ the resazurin solution (Presto Bluel) was added in each well in a volumetric ratio of 1:10 and further incubated for 4-8 h.

The results are shown in FIGS. 1 to 6. Resazurin was reduced only by activated viable cells generating a pink and fluorescent compound (resofurin) that reveals a blue gradient of reduce fluorescence in the hydrogel around the disc that correspond with cells inhibited by de immunosuppresor in a dose dependent manner generated by the passive diffusion of the compound in the hydrogel. Obtained inhibitory halos were proportional to the immunosuppressant's disc content.

As shown in the results provided, the 3D hydrogel assay is able to quantify a dose dependent inhibitory effect of cyclosporine A over human PBMC proliferation with a good linearity. These results imply the capacity of the bioassay to detect minimal variations in patient's susceptibility to different immunosuppressant compounds gradients.

It is noted, that this example, example 1, was performed in standard 6 well plates, in this support the dimensions of the radial axis is wide enough to generate the spatial dimension conditions for a proof of concept of measurable gradient conditions, but the dimensions are not optimized for a standardized measurement and the number of wells per plate completely impedes the multiscreen approximation. With this example, the only intention was to fix some of the experimental conditions which we shall later use, and constitutes a proof of concept in which different loaded amounts of the same immunosuppressant drug, in different discs, are able to generate different grades of cell inhibition measured as different inhibitory halos. Such result shall support the hypothesis that if discs loaded with different amounts of a certain drug induce different inhibitory effects in the same blood derived mononuclear cells, the same amount of drug could generate different effects in cells derived or obtained from different patients.

Example 2. Comparative Between Different Semisolid Media

Different hydrogels compositions (agarose, methylcellulose, collagen and auto assembling peptides) and percentages where prepared in X-VIVO (Lonza) cell medium. Previously isolated PBMC (activated during 24 h with antiCD3-CD28: positive control and non-activated PBMCs: negative control) were immediately added to the hydrogel-cell medium mix at a concentration in the range of 500.000 cells/ml, generating homogeneous 3D cells dispersion. After proper time for allow gelation process (30 to 90 minutes) and additional incubation period 24 or 48 hours at 37° C. and 0.5% of $CO_2$ the resazurin solution (Presto Blue®) was added in each well in a volumetric ratio of 1:10 and further incubated for 6-20 h. Activation window between activated and non-activated PBMC depends on time, hydrogel polymer chemical composition and stiffness, understood as a proportional parameter with the polymeric fraction percentage.

Figure 1:
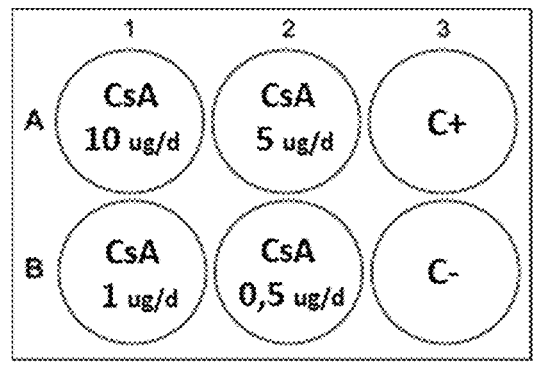
FIG. 1._6 well plate protocol design (see example 1). CsA=Cyclosporine A; ug/d=micrograms per disc;
C+=positive control (PBMC stimulated with dynabeads) C-=negative control (unstimulated PBMC).
Figure 2:
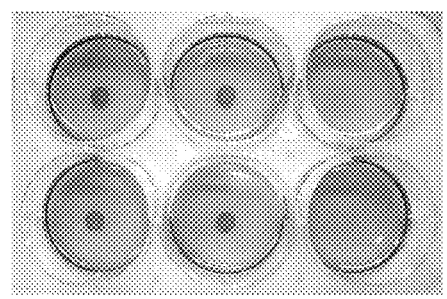
FIG. 2. Visible light 6 well plate image (Sanyo camera S1070 und E1075) of disc diffusion assay with Cyclosporine A loaded disc. Results in agarose 0.5% (A) and collagen 0.3% (B).
Figure 2:
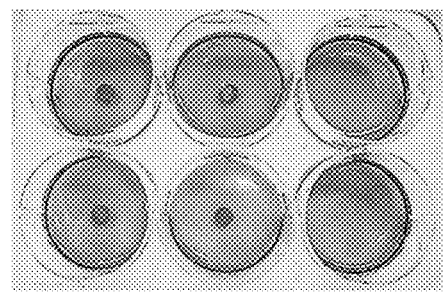
Figure 3:
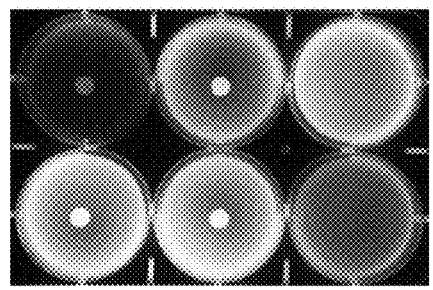
FIG. 3. Ultraviolet light 6 well plate image obtained under ultraviolet lamp exposure in a UVItec Geldoc Gel Light Imaging System with Uvidoc softwate. Results in agarose 0.5% (A) and collagen 0.3% (B).
Figure 3:
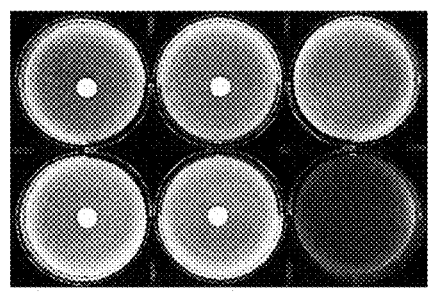
Figure 4:
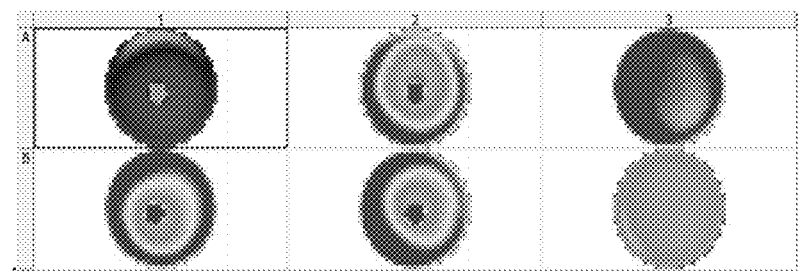
FIG. 4. Fluorescent quantification image obtained with a microplate fluorescence reader (PHERAstar® FSX Multimode Microplate Reader from BMG LABTECH). Top read, with excitation and emission wavelength adjusted to resazurin requirements Results in agarose 0.5% (A) and collagen 0.3% (B).
Figure 4:
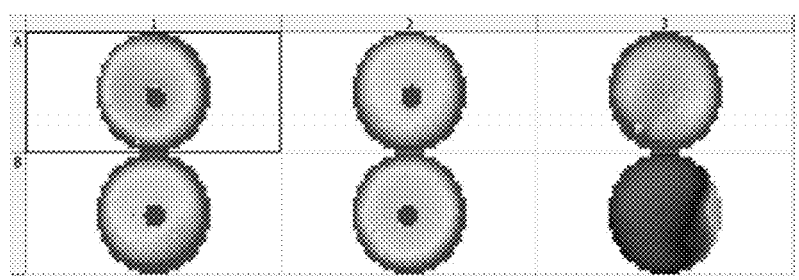
Figure 5:
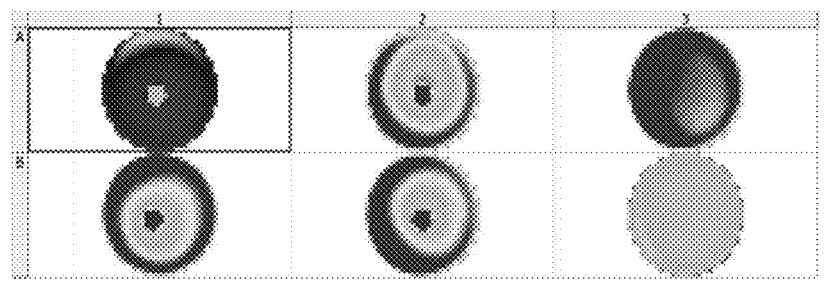
FIG. 5. Fluorescent quantification image obtained with a microplate fluorescence reader (PHERAstar® FSX Multimode Microplate Reader from BMG LABTECH). Top read, with excitation and emission wavelength adjusted to resazurin requirements. Results in agarose 0.5% (A) and collagen 0.3% (B). (Figure in gray scale).
Figure 5:
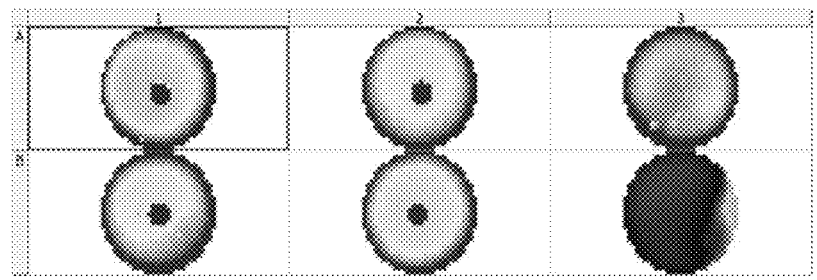
Figure 6A:
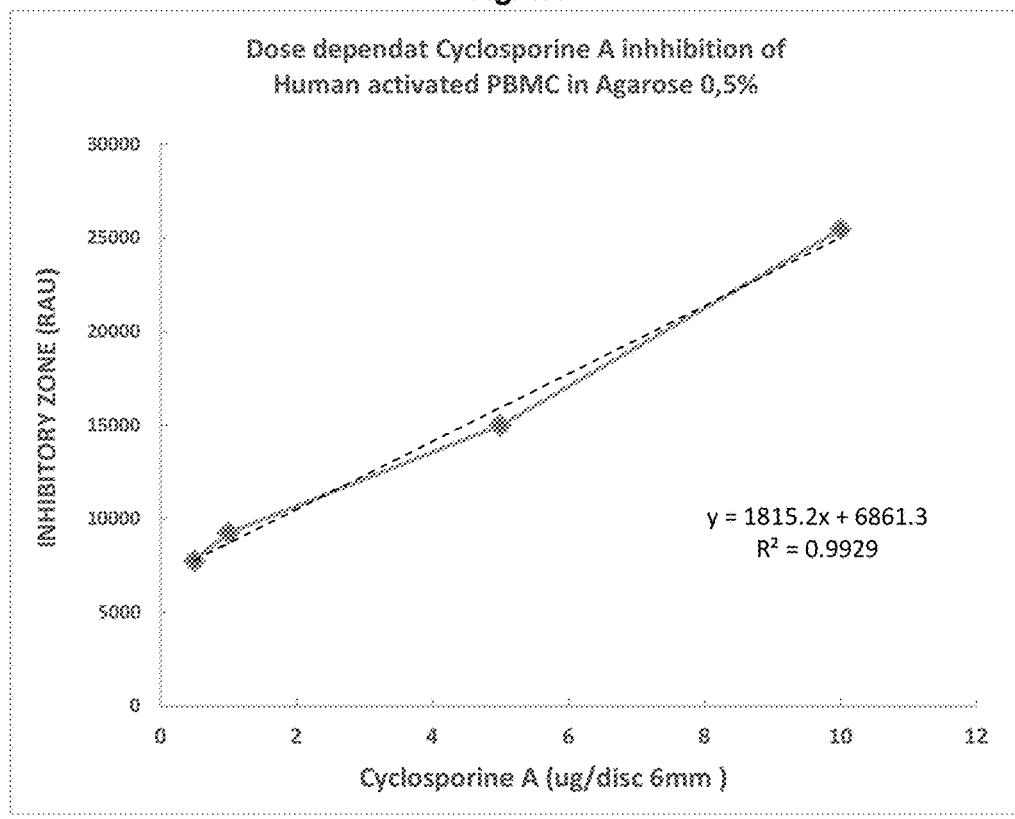
FIG. 6. Dose dependent Cyclosporine A inhibition of Human activated PBMC in a disc diffusion assay. Results in agarose 0.5% (A) and collagen 0.3% (B). RAU=Relative Area Units.
Figure 6B:
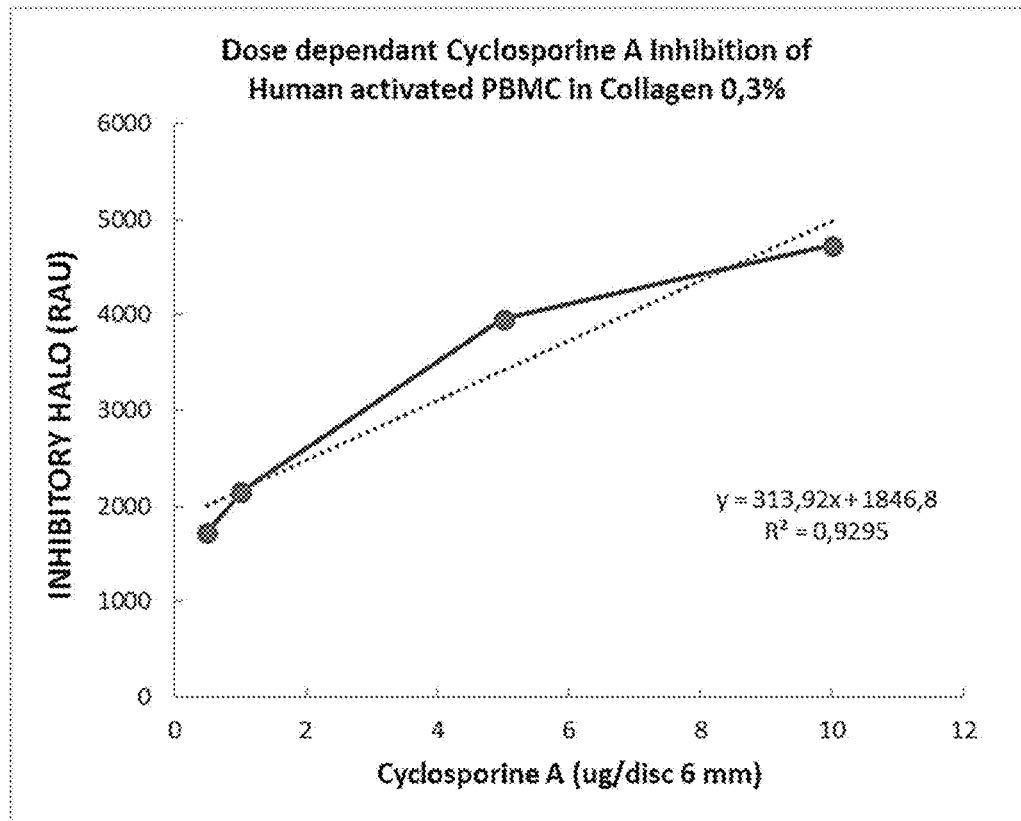
Figure 7:
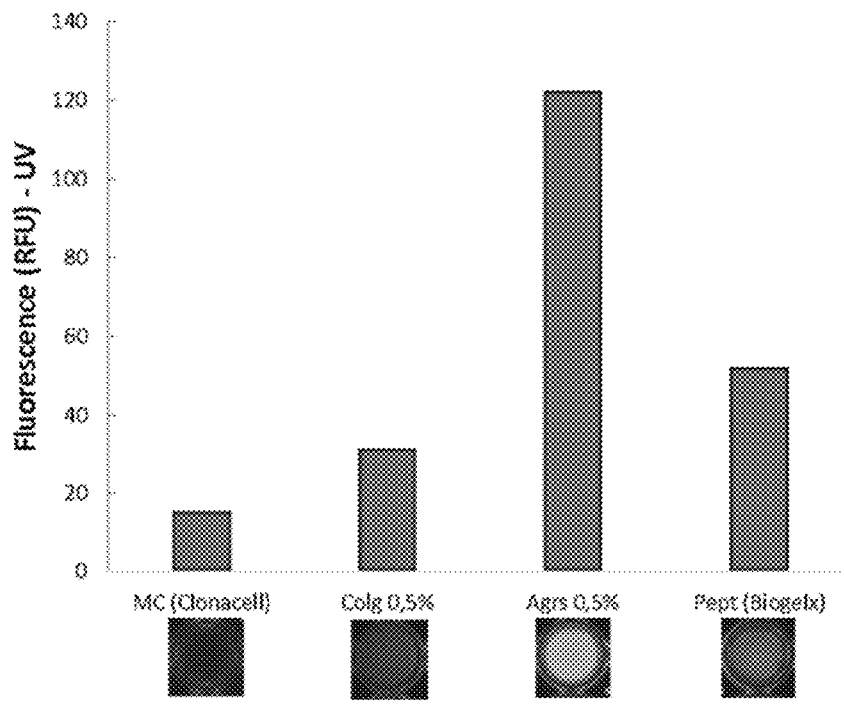
FIG. 7. Resazurin reduction fluorescent signal as cell viability/proliferative quantification of AbCD3/CD28 Dynabeads activated PBMC in different hydrogels matrices during 5 days. MC: Methylcellulose (Clonacell), Colg: Collagen, Agrs: Agarose, Pept: Auto-assembling peptide (Biogelx), RFU-UV: Relative fluorescence units under ultraviolet radiation.

As illustrated in FIG. 7, hydrogels based solely on Methylcellulose and auto-assembling peptides do not sustained viability and proliferation of activated PBMC as optimal as collagen or agarose hydrogels. These compounds are commercial ready to use products with no dilution options. In contrast, agarose 0.5% (gr/100 ml) and collagen 0.3% (gr/100 ml) generates an adequate environment for PBMC proliferation.

Figure 8:
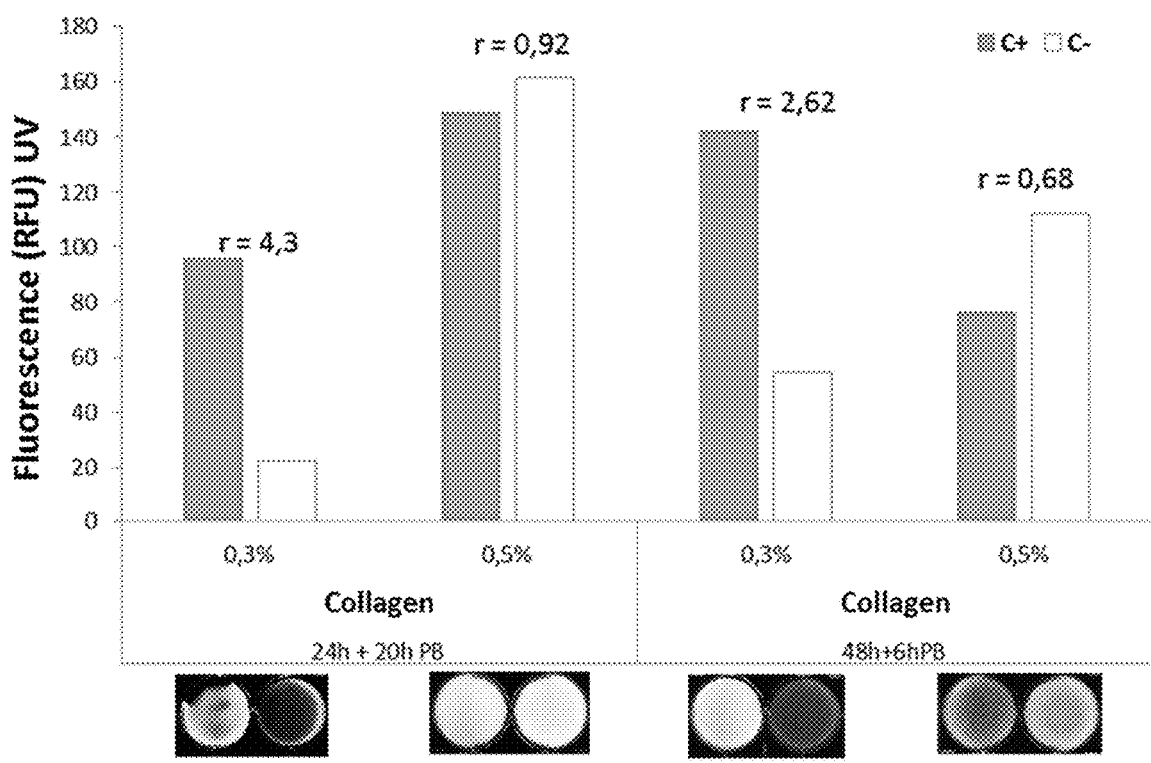
FIG. 8. Resazurin reduction fluorescent signal as cell viability/proliferative quantification of AbCD3/CD28 Dynabeads activated PBMC in different percentage collagen hydrogels matrices after 24 or 48 h of incubation.
Figure 9:
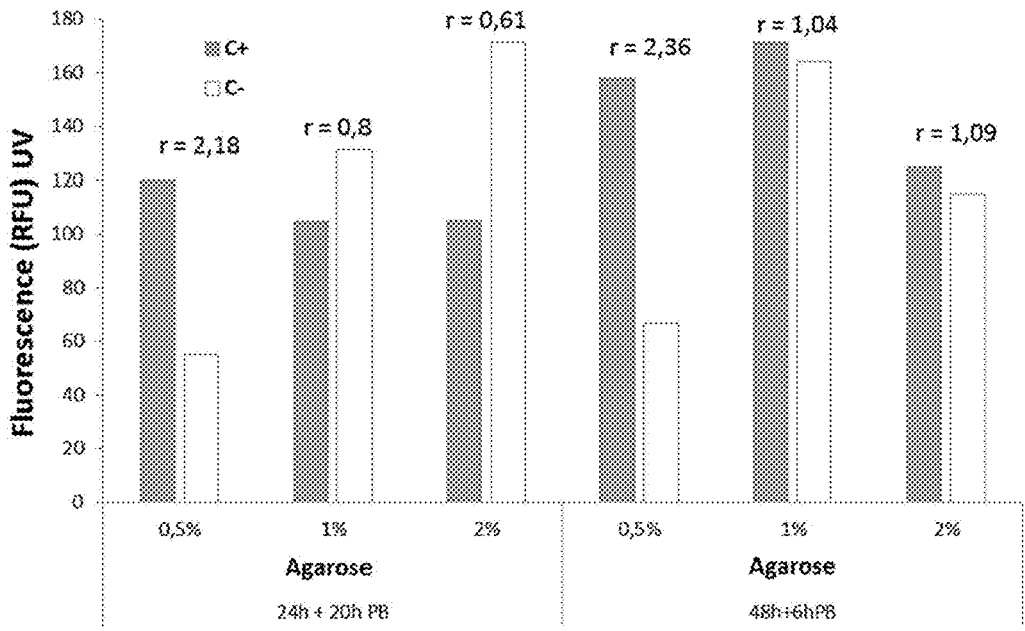
FIG. 9. Resazurin reduction fluorescent signal as cell viability/proliferative quantification of AbCD3/CD28 Dynabeads activated PBMC in different percentage agarose hydrogels matrices after 24 or 48 h of incubation.

Collagen based on dilution viability was further tested in different concentrations (see FIG. 8). As stated in FIG. 8, collagen concentrations below 5% gr/100 ml allow proliferation/viability of activated PBMC. Difference between negative and positive control increases with time, and some unspecific activation of cells was detected at short times of incubation after PBMC stimulation (around 24 h). In conclusion, percentages of collagen above 0.3% gr/100 ml are not compatible with the proposed assay.

Regarding agarose optimal percentage for PBMC culture, concentrations of agarose above 1% gr/100 ml are hard to handle during the assay due to the increasing viscosity and also exerts an inhibitory effect over PBMC proliferation/viability. In conclusion, only percentages of agarose below 0.5% gr/100 ml are compatible with the proposed assay.

Chemical composition and polymeric network density (%) severely affect immune system cells response and viability in 3D cell culture. In general, high polymeric % content inhibits cell viability and some chemical characteristics of some polymers are able to induce unspecific activation of PMBC (example: collagen). Based on these potential interactions, every new defined hydrogel composition, made by one or several different chemical polymeric compounds, could exert different effects over the disc diffusion bioassay that must be considered on case by case basis.

It is noted, that in this example, example 2, we used standard 24 and 6 well plates, with no established gradient diffusion objective. Different hydrogels were generated; including activated and inactivated PBMCs, in order to determine an activation threshold between the positive and negative controls. The results provided herein allow the identification of better hydrogel compositions, in particular to generate a wide and stable window ratio C+/C−.

Example 3. Liquid Media Dilution Methods in Microplate Format in the Context of Specific Proliferative Inhibition of Activated PBMCs Human PBMC were extracted for Buffy coat bags from blood bank volunteer donation using density gradient centrifugation in adequate hydrophilic isosmotic polysaccharide solutions with a density of 1.077 g/ml (Pancoll, PAN BIO-TECH GmbH or Ficoll, GE Healthcare) at 760 G during 20 minutes at RT. Cells were extracted with pipette from the gradient interphase and then washed in HBSS w/o Ca, Mg and Phenol red (Lonza), and resuspended in X-VIVO 15 (Lonza) medium. Obtained cells were frozen in cryovials with serum free medium (Profreeze-CDM, Lonza) DMSO (Sigma Aldrich) 7.5% and storage until use in liquid nitrogen.

A few days later, removed vials from liquid nitrogen were immediately thawed in a 37° C. water bath for 2 minutes. When cells were nearly completely thawed, vials were swipe with 70% ethanol in sterile hood. Vial content was diluted in 37° C. pre-warmed 10 ml X-VIVO medium in 15 ml falcon tubes. Centrifuge at 400G during 5 minutes. After supernatant discard, cells were re-suspended in X-VIVO medium for further count and viability quantification.

After thawing PBMCs viability was quantified by trypan blue and Neubauer chamber. Then, 35×103 viable cells per well were plated in a 96 round bottom well plate, in 100 ul of X-vivo medium in the presence or absence of proliferative stimulation with Dynabeads Human T-activator CD3/CD28 agonistic antibodies (Thermo Fisher, cat #111.32D) using a ratio 1:2 (dynabeads:PBMC). Cells were incubated at 37° C. with 5% CO2.

After 24 Hours, 1/3 serial dilutions of Cyclosporine A (Sigma) (Example of immunosuppressant drug) were added to the cells in 100 ul of X-VIVO culture medium. Cyclosporine A stock solution was prepared with DMSO or ethanol (Sigma) at 20 mg/ml and store at −20° C. till use, Stock solution aliquot was diluted in X-VIVO medium to final desired concentrations. Cyclosporine A at 100 ug/ml in this medium and conditions remains macroscopically unsolved: Highest DMSO concentration in cell culture reach 0.5% (under 1% limit of toxicity)

Resazurin solution (Presto Blue, Thermo Fisher) was added after 96 hours (24 h of incubation with Dynabeads plus additional 72 h of incubation in the presence or absence of Cyclosporine A). First 100 ul per well was removed and discarded, then presto blue solution was added in a volume ratio of 1:10 respect final volume of 150 ul per well (presto blue+X-VIVO). Final volume of each well was homogenized with 3 times multichannel pipetting in order to disaggregate cells growing mass and accelerate resazurin reduction through interaction with proliferating cells.

After 10-12 hours of incubation with presto blue, 100 ul of each well were transferred to a 96 well ELISA plate, and then absorbance at 570 and 620 nm wavelength was quantified in a robotic absorbance microplate reader (Tekan, Infinite F50). Final values were obtained as result of absorbance at 570 nm minus absorbance at 620 nm, following instructions from presto blue manufacturer (Thermo Fisher). Corrected absorbance is a direct measure of resazurin reduction to resofurin, induced by cell activity, which represents an indirect measure of cell proliferation and viability.

Figure 10:
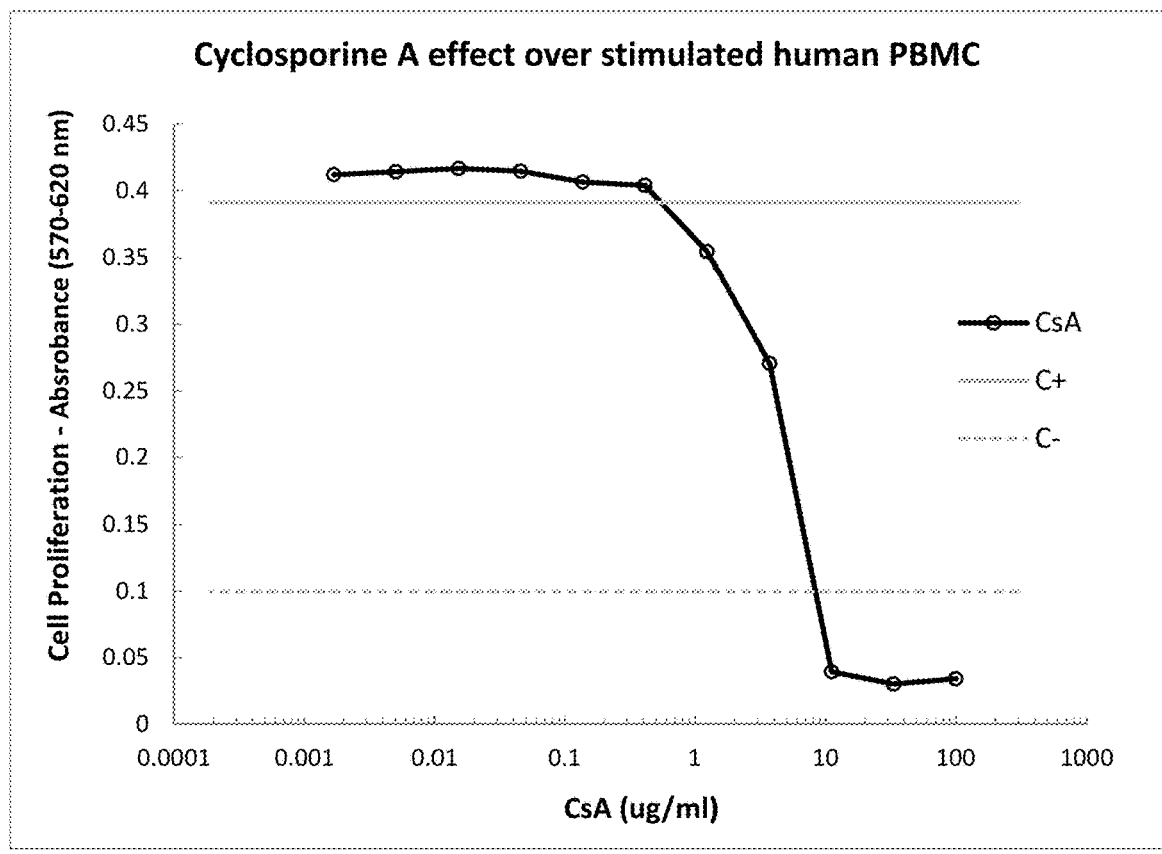
FIG. 10. Microplate liquid dilution assay of Cyclosporine A. Dose dependent Inhibition of stimulated PBMC proliferation. CsA=Cyclosporine A; C+=positive control (PBMC stimulated with dynabeads); C+=negative control (unstimulated PBMC).
Figure 11:
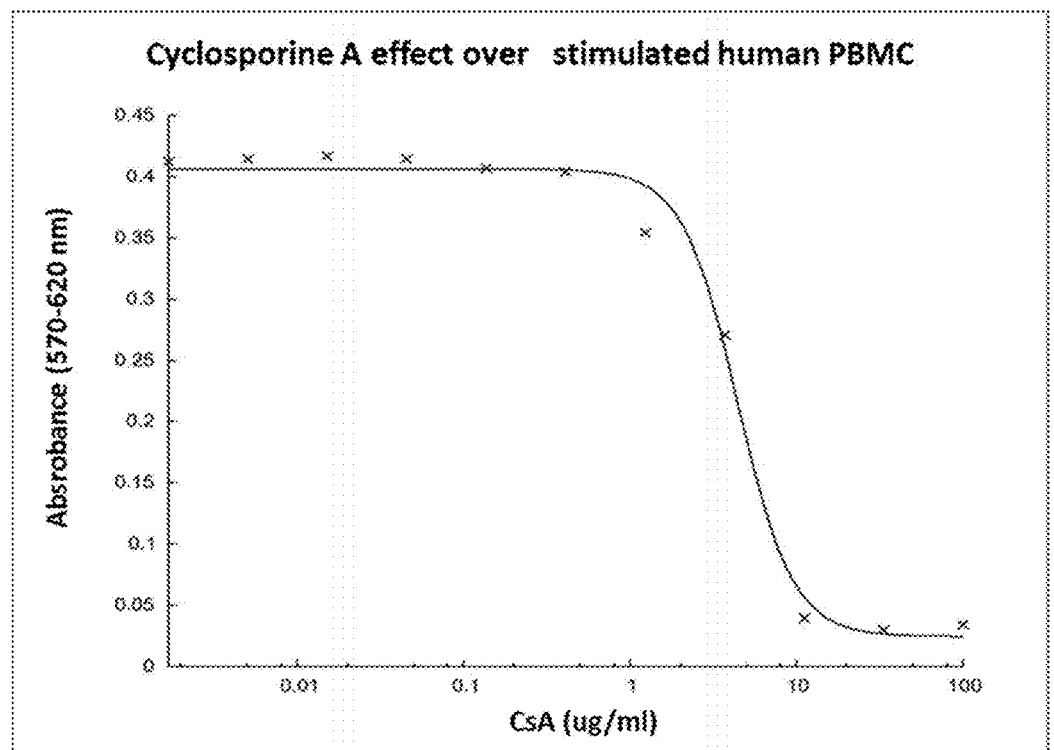
FIG. 11. Calculation of 50% Inhibitory concentration (IC50) of Cyclosporine A microplate liquid dilution assay.

The IC50 value allows biological dose-response data to be plotted and fitted to a curve to give the mid-point ligand concentration as the determination of Cylcosporine A inhibitory concentration that reduced 50% of activated PBMC proliferation. IC50 value was obtained using GNUPLOT software package. The results are shown in FIGS. 10 and 11. In the context of trying to generate a potential method for predicting and monitoring clinical response immunomodulatory therapies, the present established dilution method in microplate format presents clear disadvantages in comparison to with Hydrogel 3D format. Liquid dilution format requires almost double period of cell culture time (48 h vs 96 h) to detect response variations in activated human lymphocytes proliferation. Moreover, microplate tittering requires manual or automated serial dilutions with at least triplicates for acceptable statistical power while hydrogel format generates a passive standardized gradient process. Solubility of tested compounds (commonly hydrophobic) implies issues of organic solvents pre-dilutions, lack of reproducibility and additional manual steps; on the contrary hydrogel format implies a passive diffusion of soluble fraction of tested immunomodulatory compounds from dry delivery devices. For all of these reasons, hydrogel format presents a better profile of simplicity, potential efficiency, reduced variability and improved lead time.

It is noted that in this example, example 3, we provide results developed in standard 96 well plates in the absent of a hydrogel medium and therefore without any possibility of diffusion gradient generation.

Figure 12:
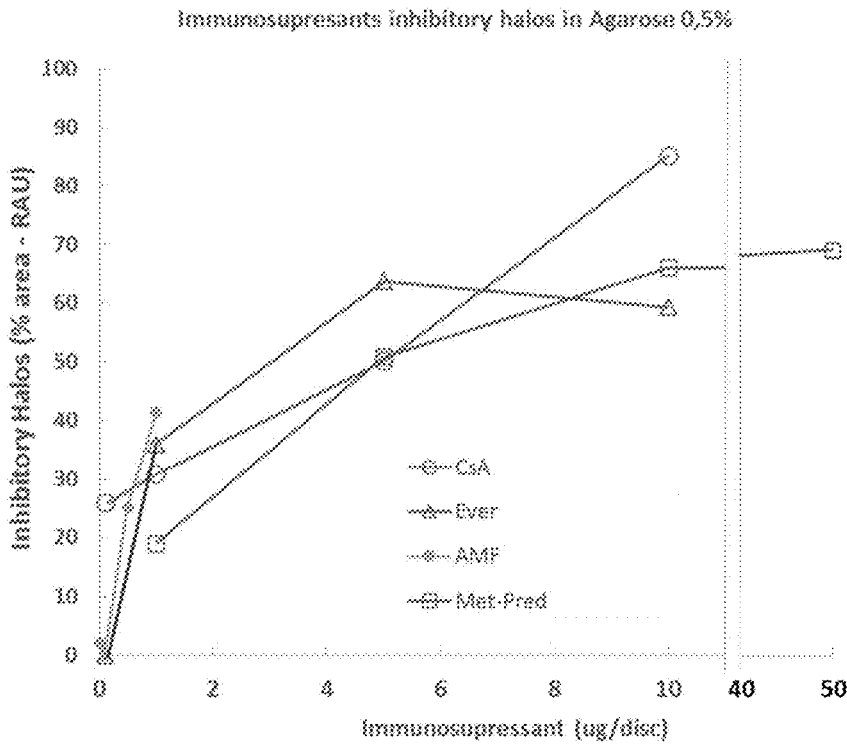
FIG. 12. Dose dependent inhibitory halos quantification of Agarose 0.5% disc diffusion assay of different immunosuppressant drugs. CsA=Cyclosporine A (Calcineurin Inhibitor); Ever=Everolimus (mTOR inhibitor), AMF=Mycophenolic Acid (DNA synthesis inhibitor), Met-Pred=Methyl Prednisolone (Glucocorticoid).
Figure 13:
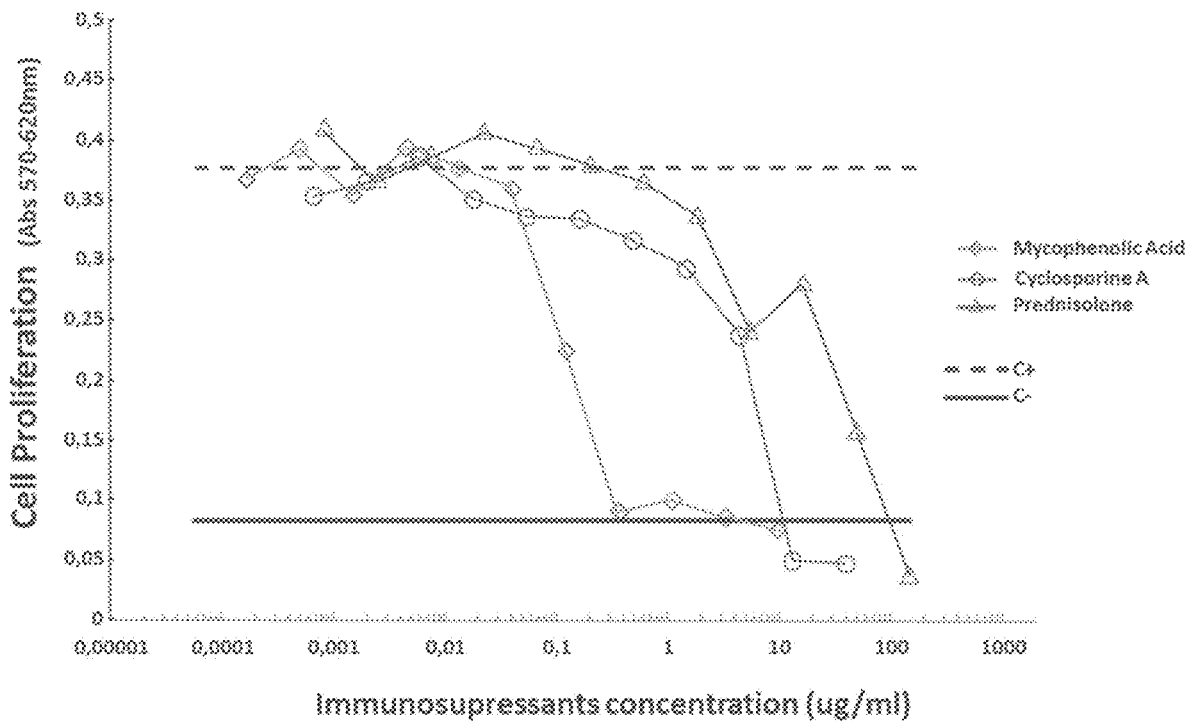
FIG. 13. Dose dependent effect of immunosupressants serial dilutions over activated human PBMCs. C+=positive control (PBMC stimulated with dynabeads) C-=negative control (unstimulated PBMC).

Example 4. Disc Diffusion Assay in Semisolid Media (Agarose 0.5%) for Different Immunosuppressant Drugs Activity Quantification Following the protocol detailed in example 1, other immunosuppressant drugs, representative of certain pharmaceutical classes, were tested in the disc diffusion assay. Mycophenolic acid (MFA) as a DNA synthesis inhibitor, Methyl Prednisolone as a glucocorticoid, Everolimus as an mTOR inhibitor and Cyclosporine A as a calcineurin inhibitor presented in example 1. Dose dependent inhibitory halos were quantified and presented in FIG. 12. Disc diffusion bioassay provides a tool able to quantified human derived PBMC activated cells susceptibility to different immunosuppressant drugs classes.

It is noted that this example, example 4, was performed in standard 6 well plates with an agarose hydrogel medium. This examples makes reference to FIG. 12, which shows how titration with different drugs loaded in discs, generates independent values (one per well) and modest titration curves (produced by using a low number of values). In addition, by using this approach, every drug analysed would require an independent plate to generate the data.

Example 5. Tittering Limitations of 48 Wells Microplate for Different Immunosuppressants Loaded Disc Doses Effect and Insufficient Gradient Over Activated PBMCs, Included in Copolymer Hydrogel (Collagen—Methyl Cellulose)

Peripheral blood mononuclear cells (PBMC) were isolated by discontinuous density gradient centrifugation on Percoll-Hanks separation medium and freeze in Profreeze Medium 7.5% DMSO until use. Previously cryopreserved PBMC were thawed with a slow defrosting process including warming the cryovials to 37° C. and adding slowly a warm washing medium. After the defrosting process, 80% of cells total were activated for 48 h with Dynabeads® at 37° C. and 5% $CO_2$ and 20% of cells were incubated in the same conditions without activation stimulus.

48 h after activation dynabeads-treated and no-treated cells were harvested and plated in in a 48-wells plate at a concentration of 500.000 cells/mL in a thermogel copolymer constituted by 30% of PureCol® EZ Gel solution 0.5% (Advance Biomatrix) plus 70% of Methyl cellulose Clona-Cell (Stem Cell Technologies) for a final hydrogel composition of collagen 0.15%. All the components of the thermogel are maintained at 4° C. to maintain the liquid state during the mixing process. Cells in the thermogel are put at 37° C. 5% CO2 for 5 minutes and then disks containing IMSs are positioned on the center of the well (extreme of the channel).

20-24 hours after the incubation, to perform a rapid quantification of cell viability Resazurin based assay was performed and 4-6 h after resazurin addition the plate was analysed with a fluorimeter. In the meantime, immunosuppressants (IMSs) stock solutions were diluted in absolute EtOH to the final desired concentration and added to a cellulose disc to allow the absorption of the IMSs and evaporation of the absolute EtOH. Cells in the thermogel are put at 37° C. 5% CO2 for 5-20 minutes and then disks containing IMSs are positioned on the center of the well (extreme of the channel). 20-24 hours after the incubation, to perform a rapid quantification of cell viability Resazurin based assay was performed and 4-6 h after resazurin addition the plate was analysed with a fluorimeter (Tecan Spark 10M).

Net fluorescent signal of each well was measured (FIG. 16-A), as well as different spatial points signal within some wells (FIG. 16-B).

It is noted that this example, example 5, was performed in standard 48 well plates, including the usage of copolymer hydrogels and discs that could potentially provide a functional diffusion gradient. Nevertheless, it is clear from the result shown in FIG. 16B that the gradients generated in reduced dimension well plates (24 to 1536) are not sufficient to adequately titrate the effect of immunosuppressive drugs on the hydrogel embedded cells. It is evident that in reduced dimension well plates (24 to 1536) with equitable 3D axes dimensions there is no possibility to generate and effective titration of the drug effect over cell response through a diffusion gradient. These results demonstrate that the proportions of the well containing the hydrogel are of pivotal relevance to obtain a gradient of diffusion that is at the same time measurable, stable and capable of providing reliable information in connection to the titration of the drug's effect. In addition, and as illustrated in FIG. 16A, the use of multi-well standard plates filled with a liquid medium, wherein each well comprises different drug concentrations, fails to provide a gradient of diffusion that is at the same time measurable, stable and capable of providing reliable information in connection to the titration of the drug's effect. In this sense, it is important to note that titration of an immunosuppressant drug's effect by using serial dilutions in standard well plates as illustrated in FIG. 16A, fails to provide a result which may be consider equivalent to those obtained through the spontaneous gradient diffusion in hydrogels having the dimensions described in the claims. In this sense, the use of serial dilutions in standard wells is based on the use of a number of arbitrary concentrations values and/or serial dilutions ratios, which shall always involve a considerable loss of information due to the lack of intermediate concentrations that can be extremely relevant to the shaping of titration curves, consequently reducing the accuracy of the titration results, and second there is a limitation in the number of potential scanning points associated with standard plates that implies one reading point per well.

Example 6. Disc Diffusion Assay in Semisolid Media (Methylcellulose/Collagen) Included in Channeled Wells Microplate for Different Immunosuppressant Drugs Activity Quantification Peripheral blood mononuclear cells (PBMC) were isolated by discontinuous density gradient centrifugation on Percoll-Hanks separation medium and freeze in Profreeze Medium 7.5% DMSO until use. Previously cryopreserved PBMC were thawed with a slow defrosting process including warming the cryovials to 37° C. and adding slowly a warm washing medium. After the defrosting process, 80% of cells total were activated for 48 h with Dynabeads® at 37° C. and 5% $CO_2$ and 20% of cells were incubated in the same conditions without activation stimulus.

48 h after activation dynabeads-treated and no-treated cells were harvested and plated in a polystyrene 12 channel reservoirs at a concentration of 500.000 cells/mL in a thermogel medium constituted by 30% of PureCol® EZ Gel solution 0.5% (Advance Biomatrix) plus 70% of Methyl cellulose ClonaCell (Stem Cell Technologies) for a final hydrogel composition of collagen 0.15%. All the components of the thermogel are maintained at 4° C. to maintain the liquid state during the mixing process. In the meantime, immunosuppressants (IMSs) stock solutions were diluted in absolute EtOH to the final desired concentration and added to a cellulose disc to allow the absorption of the IMSs and evaporation of the absolute EtOH. Cells in the thermogel are put at 37° C. 5% CO2 for 5-20 minutes and then disks containing IMSs are positioned on the extreme of the channel. 20-24 hours after the incubation, to perform a rapid quantification of cell viability Resazurin based assay was performed and 4-6 h after resazurin addition the plate was analysed with a fluorimeter (Tecan Spark 10M). Channeled wells fluorescent signal was acquired and represented in FIG. 17.

This example, example 6, is a concluding experimental procedure required to obtain titration data through diffusion gradient including plates with channeled wells (characterized by having a dimensional proportions in which one of the spatial three axes (longitudinal axis) is at least 4 times longer than the length average of the two other axes, so that the hydrogel is capable of providing a measurable and stable drug gradient flux in the major axis of the described channeled wells, wherein the channeled wells contain a hydrogel volume per channel of at least 40 l and wherein the channeled well should be covered completely by the hydrogel in its longitudinal axis and should covered at least 30% of the channeled well height), capable of providing such gradient that allow the adequate titration of the immunosuppressants effects over PBMCs' activity. This example makes reference to FIG. 17 which is performed by using 12 channeled wells (capable of providing a measurable and stable drug gradient flux in the major axis).

Example 7. Immunobiogram Results from a Clinical Study with Renal Transplanted Patients A multicenter study was conducted with a cohort of 70 renal transplant recipient patients, also 10 healthy volunteers were included for comparison purposes. The inclusion criteria consisted in men and women aged over 18 years with kidney transplant performed at least 1 year prior to inclusion. Patients present different defined and registered immunological risk profiled when included. Transplant patient clinical history includes complete recording of previous and updated immunological relevant data at the inclusion time. This data includes demographic information (donor and recipient), transplant evolution report, biochemistry of blood and urine, hemogram, detailed immunosuppressive therapy, renal function, renal biopsy results, etc.

Exclusion criteria includes age below 18 years, active infection with systemic involvement requiring antimicrobial treatment, HIV, hepatitis virus or other infectious agents that prevent proper management of clinical samples in conventional laboratory, reasonable diagnostic doubts that prevent the classification of the subject in any of the study immunological risk groups, previous history of autoimmune diseases and double transplant (renal+another organ).

Figure 20:
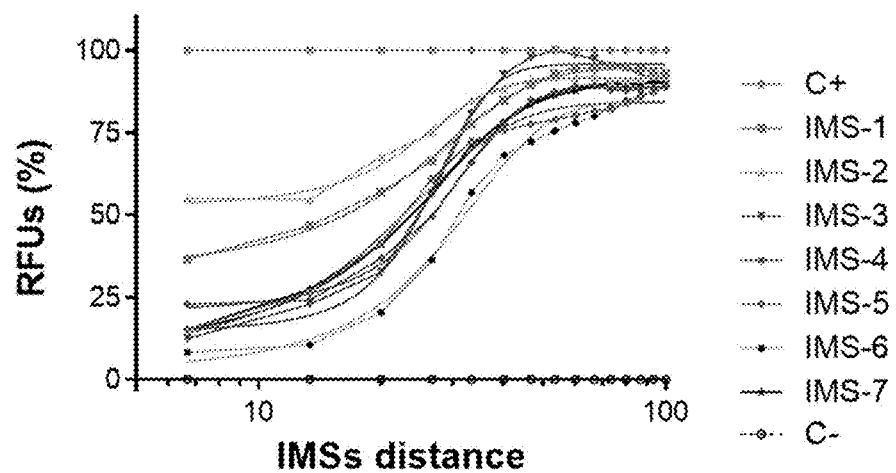
FIG. 20. Normalized representation of the inhibitory gradient effect of different immunosuppressant drugs (IMS) over a renal transplanted patient PBMCs, measured as percentage of Relative Fluorescent Units (% RFUs), included in a co-polymer hydrogel collagen-methyl cellulose. C+: positive control=100 (PBMC stimulated with dynabeads); C-: negative control=0 (unstimulated PBMC). Channeled well length was normalized from 0 (drug loaded disk edge position) to 100 (opposite channeled well edge).

Sample collection for the immunobiogram implementation consisted in two sodium heparin Vacutainer® tubes. Human PBMCs extraction from blood sample was performed using density gradient centrifugation (760 G during 15-20 minutes at RT) in adequate hydrophilic isosmotic polysaccharide solutions with a density of 1.077 g/ml (Pancoll, PAN BIOTECH GmbH or Ficoll, GE Healthcare). Cells were extracted with pipette from the gradient interphase and then washed in HBSS w/o Ca, Mg and Phenol red (Lonza), and resuspended in X-VIVO 15 (Lonza) medium. Obtained cells were frozen in cryovials with serum free medium (Profreeze-CDM, Lonza) DMSO (Sigma Aldrich) 7.5% and storage in liquid nitrogen until use. For assay execution vials were removed from liquid nitrogen were immediately thawed in a 37° C. water bath for 1-2 minutes. When cells were nearly completely thawed, vial content was diluted in 37° C. pre-warmed 10 ml X-VIVO medium in 15 ml falcon tubes. Centrifuge at 400G for 5 minutes. After the supernatant was discarded, cells were re-suspended in X-VIVO medium for further count and viability quantification. Obtained cells were divided in two groups and incubated at 37° C. and $CO_2$ 5%: one group defined as positive control (activated cells) in the presence of proliferative stimulation with Dynabeads Human T-activator CD3/CD28 agonistic antibodies (Thermo Fisher, cat #111.32D) using an approximate ratio of 1:2 (dynabeads:PBMC) and other group defined as negative control (inactivated cells) in the absence of stimulation factors. After at least 48 h cells were recover and seeded in 12 channeled well plates (characterized by having a dimensional proportions in which one of the spatial three axes (longitudinal axis) is at least 4 times longer than the length average of the two other axes, so that the hydrogel is capable of providing a measurable and stable drug gradient flux in the major axis of the described channeled wells, wherein the channeled wells contain a hydrogel volume per channel of at least 40 μl and wherein the channeled well should be covered completely by the hydrogel in its longitudinal axis and should covered at least 30% of the channeled well height) in a concentration of $5-6 \times 10^5$ cells/ml included in a copolymer hydrogel composed by methylcelullose and collagen prepared mixing at 4° C., 70% in volume of previously prepared methylcellulose solution (Clonacell™. Stemcell technologies) and 30% in volume of PureCol® EZ Gel solution 0.5% (Advance Biomatrix) for a final hydrogel composition of collagen 0.15%. After cell addition and plate distribution, gelation requires between 5-30 minutes at 37° C. After gelation, immunosuppressant loaded discs were place on the hydrogel at the edges of the channel. The plate design includes two single channels for the positive and negative control, and channels containing activated cells, as well as the positive control, but with cellulose disks of 6 mm diameter loaded with immunosuppressant drugs and placed in the edge of the remaining channels. The immunobiogram performed in this clinical study, with cells derived from patient's peripheral blood, includes independent disks containing fixed amounts of Mycophenolic acid, Cyclosporine A, Tacrolimus, Methylprednisolone, Sirolimus, Everolimus and Azathiprine (one drug per disk). Drug loaded disks were place on the edge of channels in order to stablish a gradient diffusion spatial starting point. After 24 hours of incubation at 37° C. and 5% of $CO_2$, a fluorescent indicator of cell activation/proliferation (resazurin, PrestoBlue® Cell Viability Reagent, Thermo Fisher Scientific) was added in each channel in a volumetric ratio of 1:10 (PrestoBlue:total hydrogel volume). After 2-6 hours of incubation, at 37° C. and 5% of $CO_2$, plate channels fluorescence was read in a Spark 10M™ multimode microplate reader (Tecan) obtaining results as relative fluorescent units along every plate channel distance. Data was processed and normalized for inter-patient's comparison purposes. Normalization was set from 0 to 100 for fluorescent signal window range between positive and negative control, and also set from 0 to 100 for the channel distance length between position of drug loaded disks and the opposite channels edge. From every patient and healthy donor derived PBMC every patient, immunobiogram generates a response window defined by the ratio between positive and negative control, and one titration curve per immunosuppressant drug tested through the drug diffusion gradient developed along the distance of the channeled well. The titration curves are set between the positive and negative control as shown in FIG. 20. The titration curves generate a specific analysis of cellular response to immunomodulatory drugs that could be focus on a score based on variation in potency: half-maximum inhibitory concentration (ID50), related areas over and under the curve (AOC, AUC), maximum effect ($E_{max}$), minimal effect ($E_0$), slope (Hill coefficient) or a mathematical function that includes and combines proportionally all these parameters, adapted to every drug response profile.

Figure 21:
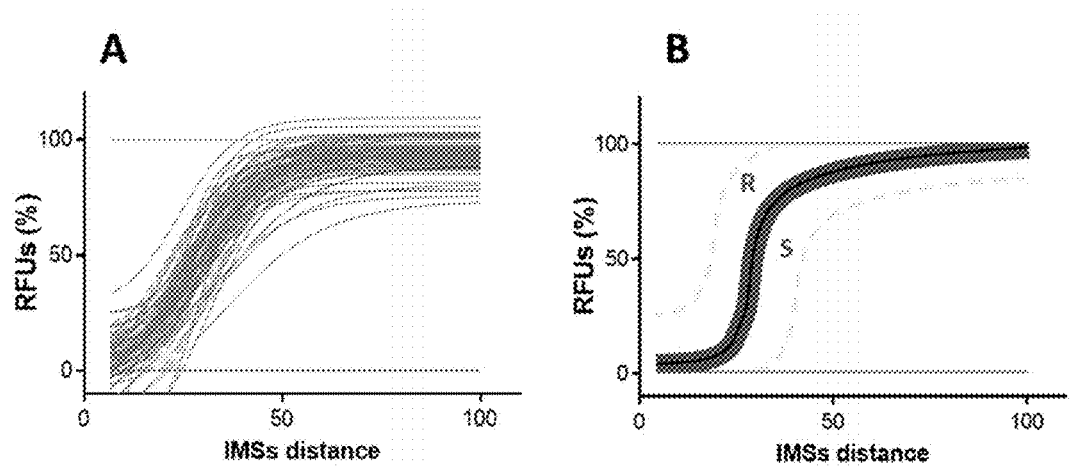
FIG. 21. Normalized representation of the inhibitory gradient curves of renal transplanted patients PBMC against Tacrolimus. Red curves indicate maximum and minimal ID50 response (A). Schematic clarification of patient curves distribution (included between dashed lines) and identification of resistance (R) and susceptible (S) patients' curves defined by spatial distribution on both side of the mean curve (continuous thick line) plus+/-deviation (blue curve area) (B).

The cumulative patient's curves per immunosuppressant drug (FIG. 21A) allow the establishment of score limits that define the relative susceptibility and resistance against a certain drug among a patients' population. The average curve of response to a specific drug, with an arbitrary range of variation define a stratification area for resistance (R) and susceptibility (S) response curves of different patients (FIG. 21B).

Based on this rationale, we developed a mathematical score to establish directly, after obtaining fluorescence results, the high or low susceptibility of a patient to an IMS. For this purpose, we first determined the most discriminant parameters between LOW and HIGH sensitivity groups as shown in FIG. 26. Next, we followed the steps identified in FIG. 27, and illustrated in FIG. 28, more than 50% of the patients in the HIGH-RISK group needed a readjustment of the treatment due to the low sensitivity of the current treatment. In addition, we noted that many low risk patients would benefit from a decrease in immunosuppression intensity because they seem to be very sensitive to medication.

Apart from the above, an additional semiquantitative score was developed considering a "clinical vision" of immunosuppressant drugs curves. In this case, instead of looking at the data from an immunosuppressant perspective, we observed data from the patient's perspective. This means that we observed the curves for ALL immunosuppressants corresponding to a single patient, which could be considered a "global sensitivity pattern" and compared this global pattern with patterns coming from other patients. Thus, the focus was putted on the patient's global response to immunosuppressants instead of a single immunosuppressant comparison with a mean response.

A semiquantitative approach was performed that distinguished three global patterns:
1) Sensitivity pattern: all immunosuppressant curves were in the higher sensitivity area of the graphical representation.
2) Double response: curves were grouped in two groups, some clearly located in the higher sensitivity area of the graphic and some in the less sensitivity area.
3) Inconsistent: curves did not offer a clear global pattern. Thus, immunosuppressants looked randomly located in the higher or lower sensitivity areas In FIG. 29, we show two real cases from a pilot study (patients 119 and 211). It is clear just by looking at the figures that global responses were very different in the two cases. Patient 119 shows what a sensitivity pattern, being sensitive to all immunosuppressant drugs. On the contrary, patient 211 shows an inconsistent pattern, being sensitive to some of the drugs and less sensitive to others. All patients were classified according to these criteria. In terms of classification, double and inconsistent responses were considered "resistant" or less sensitivity patterns. As demonstrated in FIG. 30, we were able to demonstrate that consistently with mathematical score findings, more than 50% of the patients in the HIGH-RISK group needed a readjustment of the treatment due to the low sensitivity of the current treatment. Also, many low risk patients would benefit from a decrease in immunosuppression intensity because they seem to be very sensitive to medication.

On the basis of the above, it is possible not only to stratify patients into risk categories (high-risk or low-risk patients that would benefit from treatment adjustment) (FUNCTIONALITY A), but also, a personalized recommendation can be offered (FUNCTIONALITY B). As an example of how personalization can be offered, if we take, for example, patient 211. This patient is an immunological high risk transplanted patient with a rejection episode and presence of high titers of donor antibodies. The risk of this patient of suffering from CAN or a new acute rejection episode is quite high. This patient is taking micofenolate (MMF) at high doses (1440 mg/day), tacrolimus at high doses (5 mg/day) and prednisone at standard doses, as an immunosuppressant maintenance therapy. This combination, which includes two immunosuppressant drugs at high doses, has been insufficient to prevent donor antibodies to develop and a rejection episode to occur. Looking at the Immunobiogram® graphic shown in FIG. 31, it is visually clear that the MMF curve (orange) is clearly worse, meaning less responsive, than tacrolimus (green) and prednisone (violet) curves. Therefore, it seems that patient 211 is taking high dosages of MMF medication for probably little benefit, if any. This means to assume adverse events coming from MMF with little benefits, and more important, this triple strategy is failing. It may be recommended that MMF could be changed by augmented doses of tacrolimus (if possible) and introduction of low-dose mTOR (sirolimus or everolimus).

This example confirms the clinical utility of the methodology and devices or kits of the present invention.

The invention claimed is:
1. A method to quantitatively measure the response of a patient to an immune-modulator drug, the method comprising:
a) activating peripheral blood mononuclear cells (PBMCs), total leukocytes or specific sub-populations of PBMCs, obtained from a biological sample selected from the group consisting of blood and a blood cellular derivative of the patient, either: i) though incubation with a lymphocyte activation compound selected from the group consisting of agonistic antibodies anti-CD3 (T-cell Receptor (TCR)) and anti-CD28, ionomycin and PMA (phorbol myristate acetate), a lectin, a superantigen, and a Lipopolysaccharide (LPS); or ii) through a Mix Lymphocyte Reaction, to obtain activated PBMCs;
b) obtaining a hydrogel comprising the activated PBMCs, total leukocytes or specific sub-populations of PBMCs, embedded within the hydrogel by incorporating the activated cells into a hydrogel, wherein;

the hydrogel is located in a support comprising channelled wells having dimensional proportions in which the longitudinal axis of the spatial three axes is at least 4 times longer than the length average of the two other axes, so that the hydrogel is capable of providing a measurable and stable drug gradient flux in the longitudinal axis of channelled wells, and the channelled wells contain a hydrogel volume per channel of at least 40 µl;

c) contacting the hydrogel of step b) with one or more immune-modulator drugs;

d) adding a solution comprising a compound capable of providing an absorbance, fluorescence or luminescence signal, thereby defining an inhibitory zone around a site of contact of an immunosuppressant drug with the hydrogel; and e) obtaining a quantification of the immune-modulator drug gradient formed, wherein the quantification is obtained by image acquisition or quantification of the absorbance, fluorescence or luminescence signal, wherein:

the hydrogel is formed through non-covalent crosslinking of polymer chains, wherein the total polymeric fraction represents less than 5% (5 gr/100 ml of hydrogel);

the hydrogel composition generates a non-toxic environment able to sustain cell proliferation having adequate nutritional composition and stiffness, and absent of unspecific induction of PBMCs activation; and the total polymeric fraction of the hydrogel consists of collagen, wherein the collagen content is present at below or equal to 0.3% (gr/100 ml of hydrogel).

2. The method according to claim 1, wherein the activation step a) is performed by using agonistic antibodies anti-CD3 and anti-CD28.

3. The method according to claim 1, wherein the hydrogel contains more than 95% of aqueous phase, said aqueous phase being a cell culture medium.

4. The method of claim 1, wherein the solution of step d) is a resazurin solution.

5. The method of claim 1, wherein the activating step a) comprises activating T-lymphocytes, regulatory T cells (Tregs), NK (Natural Killer cells), macrophages, B-lymphocytes, or combinations thereof.

6. The method of claim 1, wherein the activating step a) is performed by using magnetic polymer beads coated with Human T-activator CD3/CD28 agonistic antibodies.

7. The method of claim 1, wherein the channelled wells contain a hydrogel volume per channel of 40 µl to 2,800 µl.

8. A kit or device suitable for quantitatively measuring the response of a patient to an immune-modulator drug gradient using the method of claim 1, the kit comprising:

a) the support with the one or more channels comprising the hydrogel;

b) the lymphocyte activation compound;

c) a cell culture solution capable of providing the hydrogel;

d) the compound capable of providing a signal that defines an inhibitory zone around a site of contact of an immunosuppressant drug with the hydrogel; and, e) an immune-modulator drug.

9. The kit of claim 8, wherein a total polymeric fraction of the hydrogel represents less than 5% (5 gr/100 ml of hydrogel), wherein: the total polymeric fraction of the hydrogel consists of collagen, and the collagen content is present at below or equal to 0.3% (gr/100 ml of hydrogel).

10. The kit of claim 8, wherein said physical support is made of any porous material capable of releasing the immune-modulator compound once in contact with the hydrogel.

11. The kit of claim 8, wherein the lymphocyte activation compound comprises antibodies anti-CD3 and anti-CD28.

12. The kit of claim 8, wherein the compound capable of providing a signal that defines an inhibitory zone is resazurin solution.

13. The kit of claim 8, wherein an immune-modulator drug gradient formed is quantified by image acquisition or signal quantification.

* * * * *